United States Patent
Gross et al.

(10) Patent No.: US 7,678,156 B2
(45) Date of Patent: *Mar. 16, 2010

(54) COMPOSITIONS FOR TREATING KERATINIC FIBERS, METHODS OF TREATING SUCH FIBERS THEREWITH AND COMPOUNDS CONTAINED THEREIN

(75) Inventors: Wibke Gross, Düsseldorf (DE); Sandra Mausberg, Erkrath (DE); Doris Oberkobusch, Düsseldorf (DE); Horst Höffkes, Düsseldorf (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/662,792

(22) PCT Filed: Aug. 18, 2005

(86) PCT No.: PCT/EP2005/008950

§ 371 (c)(1),
(2), (4) Date: Apr. 25, 2007

(87) PCT Pub. No.: WO2006/029687

PCT Pub. Date: Mar. 23, 2006

(65) Prior Publication Data

US 2007/0287686 A1     Dec. 13, 2007

(30) Foreign Application Priority Data

Sep. 14, 2004    (DE) ................... 10 2004 044 231

(51) Int. Cl.
A61Q 5/10    (2006.01)
C07D 239/02    (2006.01)

(52) U.S. Cl. ............... 8/405; 8/406; 8/408; 8/509; 8/575; 8/576; 8/608; 544/242

(58) Field of Classification Search .............. 8/405, 8/406, 408, 509, 575, 576, 608; 544/242
See application file for complete search history.

(56) References Cited

U.S. PATENT DOCUMENTS

| | | |
|---|---|---|
| 4,865,774 A | 9/1989 | Fabry et al. |
| 4,931,218 A | 6/1990 | Schenker et al. |
| 5,061,289 A | 10/1991 | Clausen et al. |
| 5,294,726 A | 3/1994 | Behler et al. |
| 5,380,340 A | 1/1995 | Neunhoeffer et al. |
| 5,534,267 A | 7/1996 | Neunhoeffer et al. |
| 5,766,576 A | 6/1998 | Löwe et al. |
| 6,099,592 A | 8/2000 | Vidal et al. |
| 6,284,003 B1 | 9/2001 | Rose et al. |
| 6,635,090 B1 | 10/2003 | Andrean et al. |
| 7,105,032 B2 * | 9/2006 | Gross et al. ............. 8/405 |
| 2005/0144740 A1 * | 7/2005 | Gross et al. ............. 8/405 |

FOREIGN PATENT DOCUMENTS

| | | |
|---|---|---|
| AU | 730455 | 5/2000 |
| DE | 2047431 A1 | 3/1972 |
| DE | 2165913 A1 | 7/1973 |
| DE | 3723354 A | 1/1989 |
| DE | 3725030 | 2/1989 |
| DE | 3843892 | 6/1990 |
| DE | 3926344 | 2/1991 |
| DE | 4133957 | 4/1993 |
| DE | 19543988 | 5/1997 |
| DE | 10241076 A1 | 3/2004 |
| EP | 740931 | 11/1996 |
| EP | 998908 A2 | 5/2000 |
| FR | 2787707 A | 6/2000 |
| GB | 1026978 | 4/1966 |
| GB | 1153196 | 5/1969 |
| GB | 1 386 269 | 3/1975 |
| JP | 02019576 A2 | 1/1990 |

(Continued)

OTHER PUBLICATIONS

STIC Search Report dated Jul. 25, 2008.*

(Continued)

*Primary Examiner*—Eisa B Elhilo
(74) *Attorney, Agent, or Firm*—Connolly Bove Lodge & Hutz LLP

(57) ABSTRACT

Compositions suitable for treating keratinic fibers, in particular human hair, are disclosed, which compositions comprise: (i) at least one component selected from the group consisting of salt compounds of general formula I, enamine counterparts of salt compounds of general formula I, and mixtures thereof:

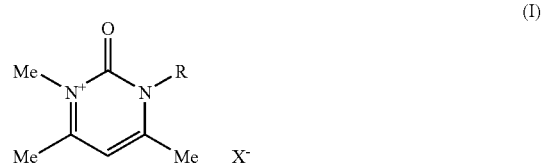

(I)

Where each Me represents a methyl group, R represents a substituent selected from the group consisting of an allyl group, a hydroxy-$(C_{2-6})$-alkyl group, a benzyl group, and substituted benzyl groups, and $X^-$ represents a physiologically compatible anion; and (ii) at least one aldehyde selected from the group consisting of 4-hydroxy-3-methoxybenzaldehyde, 3,5-dimethoxy-4-hydroxybenzaldehyde, 4-hydroxy-1-naphthaldehyde, 4-hydroxy-2-methoxybenzaldehyde, 3,4-dihydroxy-5-methoxybenzaldehyde, 3,4,5-trihydroxybenzaldehyde, 3,4-dibromo-4-hydroxybenzaldehyde, 4-hydroxy-3-nitrobenzaldehyde, 3-bromo-4-hydroxybenzaldehyde, 4-hydroxy-3-methylbenzaldehyde, 3,5-dimethyl-4-hydroxy-benzaldehyde, 5-bromo-4-hydroxy-3-methoxybenzaldehyde, 4-diethylamino-2-hydroxybenzaldehyde, 4-dimethylamino-2-methoxybenzaldehyde and mixtures thereof.

20 Claims, No Drawings

FOREIGN PATENT DOCUMENTS

| | | |
|---|---|---|
| JP | 2002047153 A2 | 2/2002 |
| WO | WO-9408969 | 4/1994 |
| WO | WO-9408970 | 4/1994 |
| WO | WO-9615765 | 5/1996 |
| WO | WO-2004022016 A | 3/2004 |

OTHER PUBLICATIONS

Zviak, *The Science of Hair Care*, Chapter 7 (pp. 284-250, and Chapter 8, pp. 264-267.

Lloyd et al., "Studies of 2-Oxo- and 2-Thioxo-1,2-dihydropyrimidinium Salts," *J. Chem. Soc. Perkin Trans I*, 1977, vol. 16, pp. 1862-1869.

Tee et al., "Synthesis of 1,3-Dialkyl-1,2-dihydro-2-oxopyrimidinium Salts by Direct Cyclization," *J. Heterocycl. Chem.*, 1974, vol. 11, No. 3, pp. 441-443.

Baumann et al., "Reaktionen der Methylenbasen von Oxazolidinonen und Pyrimidonen," *Liebigs Ann. Chem.*, 1968, vol. 717, pp. 124-136.

Chuiguk et al., "1,3-Diaryl-1,2-Dihydro-2-Oxopyrimidinium Salts and Methine Dyes Based on Them," *Ukr. Khim. Zh.* (*RussEd.*), 1982, vol. 48, No. 11, pp. 1220-1223.

\* cited by examiner

COMPOSITIONS FOR TREATING KERATINIC FIBERS, METHODS OF TREATING SUCH FIBERS THEREWITH AND COMPOUNDS CONTAINED THEREIN

CROSS-REFERENCE TO RELATED APPLICATIONS

This application is a national stage application, under 35 U.S.C. §371, of PCT/EP2005/008950 filed Aug. 18, 2005, which claims benefit of German Application No. 10 2004 044 231.2, filed Sep. 14, 2004.

BACKGROUND OF THE INVENTION

The invention relates to a substance for dyeing keratinic fibers, in particular human hair, which comprises specific 1-substituted 1,2-dihydro-3,4,6-trimethyl-2-oxopyrimidinium derivatives in combination with selected aldehydes as reactive carbonyl compound, to the use of this combination in substances for dyeing keratinic fibers, for freshening up the color or nuancing keratinic fibers which have already been dyed, and to a method of dyeing keratinic fibers, in particular human hair.

For dyeing keratinic fibers, either direct dyes or oxidation dyes, which arise as a result of oxidative coupling of one or more developer components with one another or with one or more coupler components, are generally used. Coupler and developer components are also referred to as oxidation dye precursors.

The developer components used are usually primary aromatic amines with a further free or substituted hydroxy or amino group located in the para or ortho position, diaminopyridine derivatives, heterocyclic hydrazones, 4-aminopyrazolone derivatives, and 2,4,5,6-tetraminopyrimidine and derivatives thereof.

Specific representatives are, for example, p-phenylenediamine, p-tolylenediamine, 2,4,5,6-tetraminopyrimidine, p-aminophenol, N,N-bis(2-hydroxyethyl)-p-phenylenediamine, 2-(2,5-diaminophenyl)ethanol, 2-(2,5-diaminophenoxy)ethanol, 1-phenyl-3-carboxyamido-4-aminopyrazol-5-one, 4-amino-3-methylphenol, 2-aminomethyl-4-aminophenol, 2-hydroxymethyl-4-aminophenol, 2-hydroxy-4,5,6-triaminopyrimidine, 2,4-dihydroxy-5,6-diaminopyrimidine and 2,5,6-triamino-4-hydroxypyrimidine.

The coupler components used are usually m-phenylenediamine derivatives, naphthols, resorcinol and resorcinol derivatives, pyrazolones, m-aminophenols and substituted pyridine derivatives. Suitable coupler substances are, in particular, α-naphthol, 1,5-, 2-7- and 1,7-dihydroxynaphthalene, 5-amino-2-methylphenol, m-aminophenol, resorcinol, resorcinol monomethyl ether, m-phenylenediamine, 2,4-diaminophenoxyethanol, 2-amino-4-(2-hydroxyethylamino)anisole (Lehmann's Blue), 1-phenyl-3-methylpyrazol-5-one, 2,4-dichloro-3-aminophenol, 1,3-bis(2,4-diaminophenoxy) propane, 2-chlororesorcinol, 4-chlororesorcinol, 2-chloro-6-methyl-3-aminophenol, 2-methylresorcinol, 5-methylresorcinol, 3-amino-6-methoxy-2-methylaminopyridine and 3,5-diamino-2,6-dimethoxypyridine.

With regard to further customary dye components, reference is made expressly to the "Dermatology" series, published by Ch. Culnan, H. Maibach, Verlag Marcel Dekker Inc., New York, Basle, 1986, vol. 7, Ch. Zviak, The Science of Hair Care, chapter 7, pages 248-250 (Direct Dyes) and chapter 8, pages 264-267 (Oxidation Dyes), and the "European Inventory of Cosmetic Raw Materials", 1996, published by the European Commission, obtainable in disk from the Bundesverband der deutschen Industrie- und Handelsunternehmen für Arzneimittel, Reformwaren und Körperpflegemittel e.V., Mannheim.

With oxidation dyes, although it is possible to achieve intense colorations with good fastness properties, the development of the color takes place, however, inter alia under the influence of oxidizing agents such as, for example, $H_2O_2$, which in some cases can result in damage to the fibers. The provision of oxidation hair colorations in the red range with adequate fastness properties, in particular with very good washing- and rubbing-fastnesses, continues to be problematic. Furthermore, some oxidation dye precursors or certain mixtures of oxidation dye precursors can sometimes have a sensitizing effect in people with sensitive skin. Direct dyes are applied under more gentle conditions, but their disadvantage is that the colorations often only have inadequate fastness properties.

The publication by H. Baumann et al., *Liebigs Ann. Chem.*, 1968, 717, 124-136 describes reactions of pyrimidones as methylene bases. A hair colorant comprising 1,2-dihydro-2-oxopyrimidinium derivatives or the use of the disclosed hemicyanines for dyeing keratinic fibers is not proposed here.

In the German patent application DE-A1-2047431, cationic methine dyes for dyeing anionically modified fibers, such as acidically modified polyesters or acrylonitrile polymers are described. To synthesize the cationic methine dyes, use is made, inter alia, of 3,4-dihydro-3-methyl-4-methylenequinazol-2-one and 1,3,6-trimethyl-4-methylenepyrimidin-2-one and, mandatorily, terephthalaldehyde.

The German patent application DE-A1-2165913 proposes a method of producing bleaching-out formers using photosensitive dyes. The claimed photosensitive dyes belong to the class of pyrimidone and thiopyrimidone dyes.

The German patent application DE-A1-102 41 076 proposes 1,2-dihydro-2-oxopyrimidinium derivatives in combination with reactive carbonyl compounds as substances for dyeing keratin fibers. However, these substances are still in need of improvement with regard to the fastness of the colorations thereby achieved, in particular the fastness to light and washing.

In the knowledge of the printed specification DE-A1-2165913, it is known that the dyes based on pyrimidones are photosensitive. Although it was found in DE-A1-102 41 076 that these dyes are highly suitable for dyeing hair also with regard to the light fastnesses, it was precisely the parameter of light fastness which was still in need of improvement. It is thus an object of the present invention to provide colorants for keratinic fibers, in particular human hair, which, with regard to color depth, gray coverage and fastness properties, such as, for example, light-, rubbing- and washing-fastness, and also perspiration- and cold-wave-fastness, especially washing- and light-fastness, are superior in qualitative terms to the dyes according to DE-A1-102 41 076. Moreover, the colorants must have no or only a very slight sensitization potential.

BRIEF SUMMARY OF THE INVENTION

Surprisingly, it has now been found that the compounds shown in formula I in combination with selected aldehyde derivatives are exceptionally suitable for dyeing keratinic fibers, even in the absence of oxidizing agents. They produce colorations with excellent brilliance and color depth and lead to diverse color nuances. In particular, colorations with improved washing- and light-fastness properties over a nuance range from yellow via yellow-brown, orange, brown-orange, brown, red, red-violet to blue-violet, dark blue and black are obtained. However, the use of oxidizing agents should not be excluded in principle.

The invention firstly provides a substance for dyeing keratinic fibers, in particular human hair, comprising, as component A, at least one compound according to formula I and/or its enamine form,

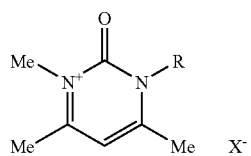

where
R is an allyl group, a hydroxy-($C_2$- to $C_6$)-alkyl group or an optionally substituted benzyl group,
$X^-$ is a physiologically compatible anion and, as component B, at least one aldehyde chosen from the group consisting of 4-hydroxy-3-methoxybenzaldehyde, 3,5-dimethoxy-4-hydroxybenzaldehyde, 4-hydroxy-1-naphthaldehyde, 4-hydroxy-2-methoxybenzaldehyde, 3,4-dihydroxy-5-methoxybenzaldehyde, 3,4,5-trihydroxybenzaldehyde, 3,5-dibromo-4-hydroxybenzaldehyde, 4-hydroxy-3-nitrobenzaldehyde, 3-bromo-4-hydroxybenzaldehyde, 4-hydroxy-3-methylbenzaldehyde, 3,5-dimethyl-4-hydroxybenzaldehyde, 5-bromo-4-hydroxy-3-methoxybenzaldehyde, 4-diethylamino-2-hydroxybenzaldehyde and 4-dimethylamino-2-methoxybenzaldehyde.

Examples of hydroxy-($C_2$- to $C_6$)-alkyl groups of the formula (I) are 2-hydroxyethyl, 2-hydroxypropyl, 3-hydroxypropyl, 4-hydroxybutyl, and 6-hydroxyhexyl. Preferred hydroxy-($C_2$- to $C_6$)-alkyl groups according to formula (I) are 2-hydroxyethyl, 2-hydroxypropyl and 3-hydroxypropyl, particularly preferably 2-hydroxypropyl and 3-hydroxypropyl.

R according to formula (I) is preferably an allyl group, a 3-hydroxypropyl group, a 2-hydroxypropyl group, a 2-hydroxyethyl group or a benzyl group.

It is preferred if $X^-$ according to formula (I) is chosen from halide, benzenesulfonate, p-toluenesulfonate, ($C_1$- to $C_4$)-alkanesulfonate, trifluoromethanesulfonate, perchlorate, 0.5 sulfate, hydrogensulfate, tetrafluoroborate, hexafluorophosphate or tetrachlorozincate. $X^-$ is particularly preferably chloride, bromide or hydrogensulfate.

The numbering of the ring-forming atoms of the heterocycle is disclosed in formula (II-1) below.

Preferably, the compounds according to formula I are chosen from the group consisting of the physiologically compatible salts of 1-allyl-1,2-dihydro-3,4,6-trimethyl-2-oxopyrimidinium, of 1,2-dihydro-1-(2-hydroxyethyl)-3,4,6-trimethyl-2-oxopyrimidinium, of 1,2-dihydro-1-(3-hydroxypropyl)-3,4,6-trimethyl-2-oxopyrimidinium and of 1-benzyl-1,2-dihydro-3,4,6-trimethyl-2-oxopyrimidinium and the enamine forms of 1-allyl-1,2-dihydro-3,4,6-trimethyl-2-oxopyrimidinium, of 1,2-dihydro-1-(2-hydroxyethyl)-3,4,6-trimethyl-2-oxopyrimidinium, of 1,2-dihydro-1-(3-hydroxypropyl)-3,4,6-trimethyl-2-oxopyrimidinium and of 1-benzyl-1,2-dihydro-3,4,6-trimethyl-2-oxopyrimidinium.

In the abovementioned salts, it is in turn preferred to select the counterion from halide, benzenesulfonate, p-toluenesulfonate, ($C_1$- to $C_4$)-alkanesulfonate, trifluoromethanesulfonate, perchlorate, 0.5 sulfate, hydrogensulfate, tetrafluoroborate, hexafluorophosphate or tetrachlorozincate, in particular from bromide, chloride, hydrogensulfate and p-toluenesulfonate.

The compounds of the formula (I) are particularly preferably chosen from the group consisting of the compounds according to formulae (II-1) to (II-12), namely the bromides, chlorides or hydrogensulfates of 1-allyl-1,2-dihydro-3,4,6-trimethyl-2-oxopyrimidinium, of 1,2-dihydro-1-(2-hydroxyethyl)-3,4,6-trimethyl-2-oxopyrimidinium, of 1,2-dihydro-1-(3-hydroxypropyl)-3,4,6-trimethyl-2-oxopyrimidinium and of 1-benzyl-1,2-dihydro-3,4,6-trimethyl-2-oxopyrimidinium and the enamine forms of these compounds. The compounds are disclosed exhaustively below in the formulae (II-1) to (II-12):

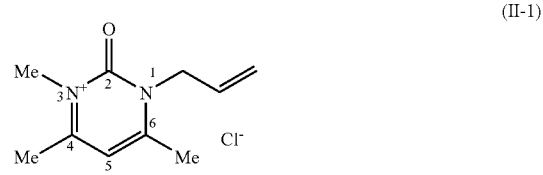

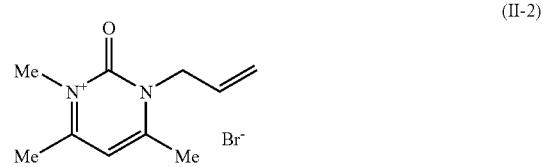

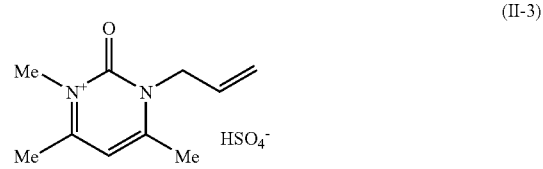

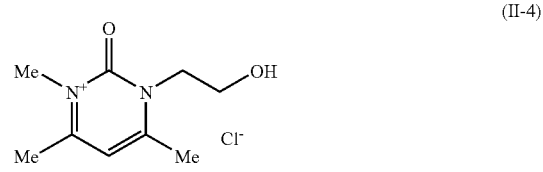

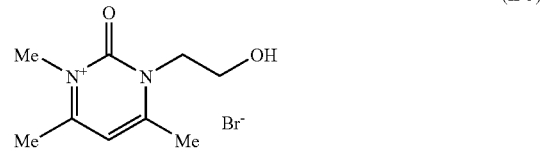

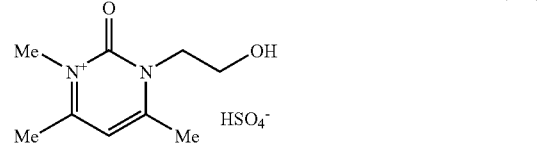

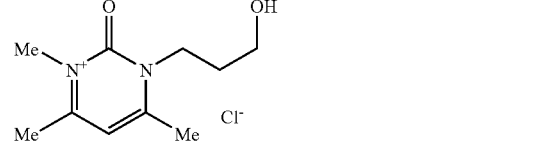

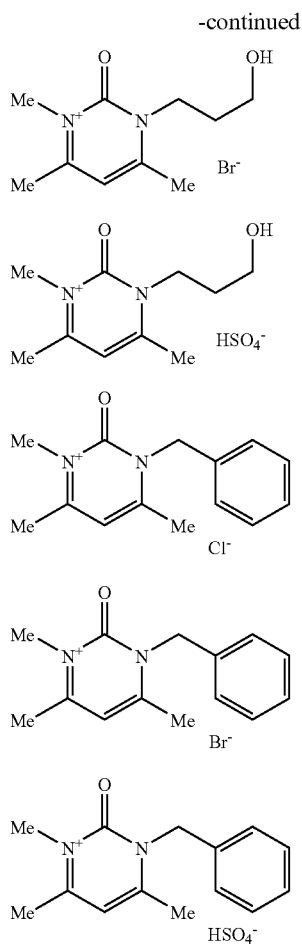

(II-8)

(II-9)

(II-10)

(II-11)

(II-12)

CH-acidic compounds are generally regarded as being those compounds which carry a hydrogen atom bonded to an aliphatic carbon atom where, on account of electron-withdrawing substituents, activation of the corresponding carbon-hydrogen bond is effected. The compounds according to the invention according to formula (I) and formulae (II-1) to (II-12) are CH-acidic compounds.

They are present in chemical equilibrium with their corresponding enamine form. With the help of a base, the corresponding enamines can be synthesized in a targeted manner from the compounds of said formulae by deprotonation at the carbon atom of the activated methyl groups in the 4 or 6 position. By way of example, this deprotonation is illustrated below. Compounds according to formulae Ia or Ib are examples of the enamine forms according to the invention of the 1,2-dihydro-3,4,6-trimethyl-2-oxopyrimidinium derivatives.

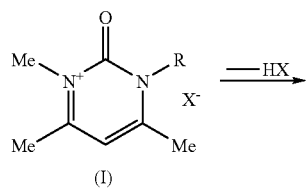

(I)

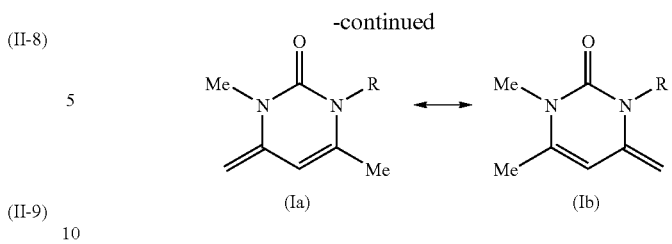

(Ia) (Ib)

DETAILED DESCRIPTION OF THE INVENTION

Keratinic fibers are understood as meaning wool, furs, feathers and, in particular, human hair. The colorants according to the invention can in principle, however, also be used for dyeing other natural fibers, such as, for example, cotton, jute, sisal, linen or silk, modified natural fibers, such as, for example, regenerated cellulose, nitro-, alkyl- or hydroxy-alkyl- or acetylcellulose.

1,2-Dihydro-2-oxopyrimidinium derivatives are generally known in the literature or commercially available. The compounds of the formula I according to the invention are novel, but can be produced by known synthesis methods according to D. Lloyd et al., *J. Chem. Soc. Perkin Trans I*, 1977, 16 1862-1869; S. T. Oswald et al., *J. Heterocycl. Chem.*, 1974, 11(3), 441-443; H. Baumann et al., *Liebigs Ann. Chem.*, 1968, 717, 124-136 and V. A. Chuiguk, *Ukr. Khim. Zh. (Russ Ed.)*, 1982, 48(11), 1220-1223.

In a second embodiment, in order to extend the color spectrum, it may be advantageous, besides at least one compound according to formula (I) as component A and at least one compound of component B, to add at least one further compound as component C to the substances according to the invention. The compound of component C is chosen from (a) CH-acidic compounds which are different from compounds of the formula (I), and/or (b) reactive carbonyl compounds which are different from the compounds of component B.

For the purposes of the invention, reactive carbonyl compounds as additional component C have at least one carbonyl group as reactive group which reacts with the CH-acidic compound according to formula I to form a carbon-carbon bond. Furthermore, according to the invention, it is also possible to use those compounds as component C in which the reactive carbonyl group is derivatized or masked in such a way that the reactivity of the carbon atom of the derivatized carbonyl group toward the CH-acidic compounds of the formula I is always present. These derivatives are preferably addition compounds a) of amines and derivatives thereof with formation of imines or oximes as addition compound b) of alcohols with formation of acetals or ketals as addition compound c) of water with formation of hydrates as addition compound (component B is in this case c) derived from an aldehyde ab)

onto the carbon atom of the carbonyl group of the reactive carbonyl compound.

The additional CH-acidic compounds of component C are preferably chosen from the group consisting of salts, formed with physiologically compatible anions, in particular p-toluenesulfonates, methanesulfonates, hydrogensulfates, tetrafluoroborates and halides, such as the chlorides, bromides and iodides, of 1,4-dimethylquinolinium, 1-ethyl-4-methylquinolinium, 1-ethyl-2-methylquinolinium, 1,2,3,3-tetramethyl-3H-indolium, 2,3-dimethylbenzothiazolium, 2,3- dimethylnaphtho[1,2-d]thiazolium, 3-ethyl-2-methylnaphtho[1,2-d]thiazolium, 3-ethyl-2-methylbenzoxazolium, 1,2,3-trimethylquinoxalinium, 3-ethyl-2-methylbenzothiazolium, 1,2-dihydro-1,3,4,6-tetramethyl-2-oxopyrimidinium, 1,2-dihydro-1,3,4-trimethyl-2-oxopyrimidinium, 1,2-dihydro-4,6-dimethyl-1,3-dipropyl-2-oxopyrimidinium, 1,2-dihydro-1,3,4,6-tetramethyl-2-thioxopyrimidinium, 1,2-dihydro-1,3,4,5,6-pentamethyl-2-oxopyrimidinium, 2,5-dimethyl-3-(2-propenyl)-1,3,4-thiadiazolium, 3-ethyl-2,5-dimethyl-1,3,4-thiadiazolium, 1,2-dimethylquinolinium and 1,3,3-trimethyl-2-methyleneindoline (Fischer's base), oxindole, 3-methyl-1-phenylpyrazolin-5-one, indane-1,2-dione, indane-1,3-dione, indan-1-one, 2-amino-4-imino-1,3-thiazoline hydrochloride, benzoylacetonitrile, 3-dicyanomethyleneindan-1-one, 2-(2-furanoyl)acetonitrile, 2-(2-theonyl)acetonitrile, 2-(cyanomethyl)benzimidazole, 2-(cyanomethyl)benzothiazole and 2-(2,5-dimethyl-3-furanoyl)acetonitrile.

Preferred additional reactive carbonyl compounds of component C are chosen from the group consisting of benzaldehyde and its derivatives, naphthaldehyde and its derivatives, cinnamaldehyde and its derivatives, 2,3,6,7-tetrahydro-1H,5H-benzo[ij]quinolizine-9-carboxaldehyde, 2,3,6,7-tetrahydro-8-hydroxy-1H,5H-benzo[ij]quinolizine-9-carboxaldehyde, N-ethylcarbazole-3-aldehyde, 2-formylmethylene-1,3,3-trimethylindoline (Fischer's aldehydes or tribase aldehydes), 2-indolealdehyde, 3-indolealdehyde, 1-methylindole-3-aldehyde, 2-methylindole-3-aldehyde, 2-(1',3',3'-trimethyl-2-indolinylidene)acetaldehyde, 1-methylpyrrole-2-aldehyde, 4-pyridinealdehyde, 2-pyridinealdehyde, 3-pyridinealdehyde, pyridoxal, antipyrine-4-aldehyde, furfural, 5-nitrofurfural, 2-thenoyltrifluoroacetone, chromone-3-aldehyde, 3-(5'-nitro-2'-furyl)acrolein, 3-(2'-furyl)acrolein and imidazole-2-aldehyde, 5-(4-dimethylaminophenyl)penta-2-4-dienal, 5-(4-diethylaminophenyl)penta-2,4-dienal, 5-(4-methoxyphenyl)penta-2,4-dienal, 5-(3,4-dimethoxyphenyl)penta-2,4-dienal, 5-(2,4-dimethoxyphenyl)penta-2,4-dienal, 5-(4-piperidinophenyl)penta-2,4-dienal, 5-(4-morpholinophenyl)penta-2,4-dienal, 5-(4-pyrrolidinophenyl)penta-2,4-dienal, 5-(4-dimethylamino-1-naphthyl)penta-3,5-dienal, 9-methyl-3-carbazolealdehyde, 9-ethyl-3-carbazolealdehyde, 3-acetylcarbazole, 3,6-diacetyl-9-ethylcarbazole, 3-acetyl-9-methylcarbazole, 1,4-dimethyl-3-carbazolealdehyde, 1,4,9-trimethyl-3-carbazolealdehyde, 6-nitropiperonal, 2-nitropiperonal, 5-nitrovanillin, 2,5-dinitrosalicylaldehyde, 5-bromo-3-nitrosalicylaldehyde, 3-nitro-4-formylbenzenesulfonic acid, 4-formyl-1-methylpyridinium, 2-formyl-1-methylpyridinium, 4-formyl-1-ethylpyridinium, 2-formyl-1-ethylpyridinium, 4-formyl-1-benzylpyridinium, 2-formyl-1-benzylpyridinium, 4-formyl-1,2-dimethylpyridinium, 4-formyl-1,3-dimethylpyridinium, 4-formyl-1-methylquinolinium, 2-formyl-1-methylquinolinium, 5-formyl-1-methylquinolinium, 6-formyl-1-methylquinolinium, 7-formyl-1-methylquinolinium, 8-formyl-1-methylquinolinium, 5-formyl-1-ethylquinolinium, 6-formyl-1-ethylquinolinium, 7-formyl-1-ethylquinolinium, 8-formyl-1-ethylquinolinium, 5-formyl-1-benzylquinolinium, 6-formyl-1-benzylquinolinium, 7-formyl-1-benzylquinolinium, 8-formyl-1-benzylquinolinium, 5-formyl-1-allylquinolinium, 6-formyl-1-allylquinolinium, 7-formyl-1-allylquinolinium and 8-formyl-1-allylquinolinium benzenesulfonate, p-toluenesulfonate, methanesulfonate, perchlorate, sulfate, chloride, bromide, iodide, tetrachlorozincate, methylsulfate, trifluoromethanesulfonate, tetrafluoroborate, isatin, 1-methylisatin, 1-allylisatin, 1-hydroxymethylisatin, 5-chloroisatin, 5-methoxyisatin, 5-nitroisatin, 6-nitroisatin, 5-sulfoisatin, 5-carboxylsatin, quinisatin, 1-methylquinisatin, and any mixtures of the above compounds.

The derivatives of the benzaldehydes, naphthaldehydes and cinnamaldehydes of the reactive carbonyl compound according to component C are preferably chosen from coniferylaldehyde, 2-methoxybenzaldehyde, 3-methoxybenzaldehyde, 4-methoxybenzaldehyde, 2-ethoxybenzaldehyde, 3-ethoxybenzaldehyde, 4-ethoxybenzaldehyde, 4-hydroxy-2,3-dimethoxybenzaldehyde, 4-hydroxy-2,5-dimethoxybenzaldehyde, 4-hydroxy-2,6-dimethoxybenzaldehyde, 4-hydroxy-2-methylbenzaldehyde, 4-hydroxy-2,3-dimethylbenzaldehyde, 4-hydroxy-2,5-dimethylbenzaldehyde, 4-hydroxy-2,6-dimethylbenzaldehyde, 3,5-diethoxy-4-hydroxybenzaldehyde, 2,6-diethoxy-4-hydroxybenzaldehyde, 3-hydroxy-4-methoxybenzaldehyde, 2-hydroxy-4-methoxybenzaldehyde, 2-ethoxy-4-hydroxybenzaldehyde, 3-ethoxy-4-hydroxybenzaldehyde, 4-ethoxy-2-hydroxybenzaldehyde, 4-ethoxy-3-hydroxybenzaldehyde, 2,3-dimethoxybenzaldehyde, 2,4-dimethoxybenzaldehyde, 2-5-dimethoxybenzaldehyde, 2,6-dimethoxybenzaldehyde, 3,4-dimethoxybenzaldehyde, 3,5-dimethoxybenzaldehyde, 2,3,4-trimethoxybenzaldehyde, 2,3,5-trimethoxybenzaldehyde, 2,3,6-trimethoxybenzaldehyde, 2,4,6-trimethoxybenzaldehyde, 2,4,5-trimethoxybenzaldehyde, 2,5,6-trimethoxybenzaldehyde, 2-hydroxybenzaldehyde, 3-hydroxybenzaldehyde, 4-hydroxybenzaldehyde, 2,3-dihydroxybenzaldehyde, 2,4-dihydroxybenzaldehyde, 2,4-dihydroxy-3-methylbenzaldehyde, 2,4-dihydroxy-5-methylbenzaldehyde, 2,4-dihydroxy-6-methylbenzaldehyde, 2,4-dihydroxy-3-methoxybenzaldehyde, 2,4-dihydroxy-5-methoxybenzaldehyde, 2,4-dihydroxy-6-methoxybenzaldehyde, 2,5-dihydroxybenzaldehyde, 2,6-dihydroxybenzaldehyde, 3,4-dihydroxybenzaldehyde, 3,4-dihydroxy-2-methylbenzaldehyde, 3,4-dihydroxy-5-methylbenzaldehyde, 3,4-dihydroxy-6-methylbenzaldehyde, 3,4-dihydroxy-2-methoxybenzaldehyde, 3,5-dihydroxybenzaldehyde, 2,3,4-trihydroxybenzaldehyde, 2,3,5-trihydroxybenzaldehyde, 2,3,6-trihydroxybenzaldehyde, 2,4,6-trihydroxybenzaldehyde, 2,4,5-trihydroxybenzaldehyde, 2,5,6-trihydroxybenzaldehyde, 4-dimethylaminobenzaldehyde, 4-diethylaminobenzaldehyde, 4-dimethylamino-2-hydroxybenzaldehyde, 4-pyrrolidinobenzaldehyde, 4-morpholinobenzaldehyde, 2-morpholinobenzaldehyde, 4-piperidinobenzaldehyde, 3,5-dichloro-4-hydroxybenzaldehyde, 4-hydroxy-3,5-diiodobenzaldehyde, 3-chloro-4-hydroxybenzaldehyde, 5-chloro-3,4-dihydroxybenzaldehyde, 5-bromo-3,4-dihydroxybenzaldehyde, 3-chloro-4-hydroxy-5-methoxybenzaldehyde, 4-hydroxy-3-iodo-5-methoxybenzaldehyde, 2-methoxy-1-naphthaldehyde, 4-methoxy-1-naphthaldehyde, 2-hydroxy-1-naphthaldehyde, 2,4-dihydroxy-1-naphthaldehyde, 4-hydroxy-3-methoxy-1-naphthaldehyde, 2-hydroxy-4-methoxy-1-naphthaldehyde, 3-hydroxy-4-methoxy-1-naphthaldehyde, 2,4-dimethoxy-1-naphthaldehyde, 3,4-dimethoxy-1-naphthaldehyde, 4-dimethylamino-1-naphthaldehyde, 2-nitrobenzaldehyde, 3-nitrobenzaldehyde, 4-nitrobenzaldehyde, 4-methyl-3-nitrobenzaldehyde, 3-hydroxy-4-nitrobenzaldehyde, 5-hydroxy-2-nitrobenzaldehyde, 2-hydroxy-5-nitrobenzaldehyde, 2-hydroxy-3-nitrobenzaldehyde, 2-fluoro-3-nitrobenzaldehyde, 3-methoxy-2-nitrobenzaldehyde, 4-chloro-3-nitrobenzaldehyde, 2-chloro-6-nitrobenzaldehyde, 5-chloro-2-nitrobenzaldehyde, 4-chloro-2-nitrobenzaldehyde, 2,4-dinitrobenzaldehyde, 2,6-dinitrobenzaldehyde, 2-hydroxy-3-methoxy-5-nitrobenzaldehyde, 4,5-dimethoxy- 2-nitrobenzaldehyde, 6-nitropiperonal, 2-nitropiperonal, 5-nitrovanillin, 2,5-dinitrosalicylaldehyde, 5-bromo-3-nitrosalicylaldehyde, 4-nitro-1-naphthaldehyde, 2-nitrocinnamaldehyde, 3-nitrocinnamaldehyde, 4-nitrocinnamaldehyde, 4-dimethylaminocinnamaldehyde, 2-dimethylaminobenzaldehyde, 2-chloro-4-dimethylaminobenzaldehyde, 4-dimethylamino-2-methylbenzaldehyde, 4-diethylaminocinnamaldehyde, 4-dibutylaminobenzaldehyde, 4-diphenylaminobenzaldehyde, 4-(1-imidazolyl)benzaldehyde and piperonal. These representatives are at the same time the particularly preferred additional reactive carbonyl compounds of component C.

The printed specifications EP-A2-998 908 and JP-A2-2002047153 disclose to the person skilled in the art hair colorants which comprise, inter alia, as direct dye, at least one compound with a 1,2-dihydro-2-oxopyrimidinium radical. In a third embodiment, the colorant additionally comprises at least one reaction product (referred to below as reaction product RP) of a 1,2-dihydro-2-oxopyrimidinium derivative of the formula I and a compound of component B as direct dye. Such reaction products RP can be obtained, for example, by heating the two reactants in aqueous neutral to weakly alkaline medium, where the reaction products RP either precipitate out of the solution as solid or are isolated therefrom by evaporating the solution. There is also the option of synthesizing the reaction products according to the literature H. Baumann et al., *J. Liebigs Ann. Chem.*, 1968, 717, 124-136 or DE-A1-2165913.

For the synthesis of the reaction products RP, molar ratios of component B to the compound according to formula I of from about 1:1 to about 2:1 may be useful.

The abovementioned compounds with the formula I, the compounds of component B, component C, and the reaction products RP are in each case preferably used in an amount of from 0.03 to 65 mmol, in particular from 1 to 40 mmol, based on 100 g of the total colorant.

In addition, the substances according to the invention can comprise at least one developer component and optionally at least one coupler component as oxidation dye precursors.

According to the invention, it may be preferred to use a p-phenylenediamine derivative or one of its physiologically compatible salts as developer component. Particular preference is given to p-phenylenediamine derivatives of the formula (E1)

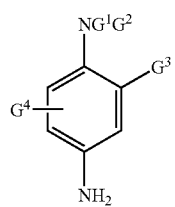
(E1)

where
$G^1$ is a hydrogen atom, a $C_1$- to $C_4$-alkyl radical, a $C_1$- to $C_4$-monohydroxyalkyl radical, a $C_2$- to $C_4$-polyhydroxyalkyl radical, a $(C_1$- to $C_4)$-alkoxy-$(C_1$- to $C_4)$-alkyl radical, a 4'-aminophenyl radical or a $C_1$- to $C_4$-alkyl radical which is substituted by a nitrogen-containing group, a phenyl radical or a 4'-aminophenyl radical;

$G^2$ is a hydrogen atom, a $C_1$- to $C_4$-alkyl radical, a $C_1$- to $C_4$-monohydroxyalkyl radical, a $C_2$- to $C_4$-polyhydroxyalkyl radical, a $(C_1$- to $C_4)$-alkoxy-$(C_1$- to $C_4)$-alkyl radical or a $C_1$- to $C_4$-alkyl radical which is substituted by a nitrogen-containing group;

$G^3$ is a hydrogen atom, a halogen atom, such as a chlorine atom, bromine atom, iodine atom or fluorine atom, a $C_1$- to $C_4$-alkyl radical, a $C_1$- to $C_4$-monohydroxyalkyl radical, a $C_2$- to $C_4$-polyhydroxyalkyl radical, a $C_1$- to $C_4$-hydroxyalkoxyradical, a $C_1$ to $C_4$-acetylaminoalkoxy radical, a $C_1$- to $C_4$-mesylaminoalkoxy radical or a $C_1$- to $C_4$-carbamoylaminoalkoxy radical;

$G^4$ is a hydrogen atom, a halogen atom or a $C_1$- to $C_4$-alkyl radical or if $G^3$ and $G^4$ are in the ortho position relative to one another, they can together form a bridging α, ω-alkylenedioxo group, such as, for example, an ethylenedioxy group.

Examples of the $C_1$- to $C_4$-alkyl radicals specified as substituents in the compounds according to the invention are the groups methyl, ethyl, propyl, isopropyl and butyl. Ethyl and methyl are preferred alkyl radicals. $C_1$- to $C_4$-alkoxy radicals preferred according to the invention are, for example, a methoxy or an ethoxy group. In addition, preferred examples of a $C_1$- to $C_4$-hydroxyalkyl group which can be mentioned are a hydroxymethyl group, a 2-hydroxyethyl group, a 3-hydroxypropyl group or a 4-hydroxybutyl group. A 2-hydroxyethyl group is particularly preferred. A particularly preferred $C_2$- to $C_4$-polyhydroxyalkyl group is the 1,2-dihydroxyethyl group. Examples of halogen atoms according to the invention are F, Cl or Br atoms, Cl atoms are very particularly preferred. According to the invention, the other terms used are derived from the definitions given here. Examples of nitrogen-containing groups of the formula (E1) are, in particular, the amino groups, $C_1$- to $C_4$-monoalkylamino groups, $C_1$- to $C_4$-dialkylamino groups, $C_1$- to $C_4$-trialkylammonium groups, $C_1$- to $C_4$-monohydroxyalkylamino groups, imidazolinium and ammonium.

Particularly preferred p-phenylenediamines of the formula (E1) are chosen from p-phenylenediamine, p-tolylenediamine, 2-chloro-p-phenylenediamine, 2,3-dimethyl-p-phenylenediamine, 2,6-dimethyl-p-phenylenediamine, 2,6-diethyl-p-phenylenediamine, 2,5-dimethyl-p-phenylenediamine, N,N-dimethyl-p-phenylenediamine, N,N-diethyl-p-phenylenediamine, N,N-dipropyl-p-phenylenediamine, 4-amino-3-methyl-(N,N-diethyl)aniline, N,N-bis(β-hydroxyethyl)-p-phenylenediamine, 4-N,N-bis(β-hydroxyethyl)amino-2-methylaniline, 4-N,N-bis(β-hydroxyethyl)amino-2-chloroaniline, 2-(β-hydroxyethyl)-p-phenylenediamine, 2-(α,β-dihydroxyethyl)-p-phenylenediamine, 2-fluoro-p-phenylenediamine, 2-isopropyl-p-phenylenediamine, N-(β-hydroxypropyl)-p-phenylenediamine, 2-hydroxymethyl-p-phenylenediamine, N,N-dimethyl-3-methyl-p-phenylenediamine, N,N-(ethyl,β-hydroxyethyl)-p-phenylenediamine, N-(β,γ-dihydroxypropyl)-p-phenylenediamine, N-(4'-aminophenyl)-p-phenylenediamine, N-phenyl-p-phenylenediamine, 2-(β-hydroxyethyloxy)-p-phenylenediamine, 2-(β-acetylaminoethyloxy)-p-phenylenediamine, N-(β-methoxyethyl)-p-phenylenediamine, N-(4-amino-3-methylphenyl)-N-[3-(1H-imidazol-1-yl)propyl]amine and 5,8-diaminobenzo-1,4-dioxane, and their physiologically compatible salts.

According to the invention, very particularly preferred p-phenylenediamine derivatives of the formula (E1) are p-phenylenediamine, p-tolylenediamine, 2-(β-hydroxyethyl)-p-phenylenediamine, 2-(α,β-dihydroxyethyl)-p-phenylenediamine and N,N-bis(β-hydroxyethyl)-p-phenylenediamine.

According to the invention, it may also be preferred to use, as developer component, compounds which contain at least two aromatic nuclei which are substituted by amino and/or hydroxyl groups.

Among the binuclear developer components which can be used in the coloring compositions according to the invention, mention may be made in particular of the compounds which conform to the following formula (E2), and their physiologically compatible salts:

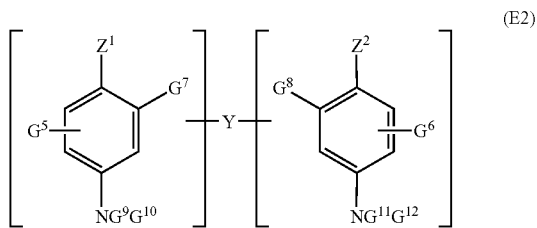

where:
- $Z^1$ and $Z^2$, independently of one another, are a hydroxyl or $NH_2$ radical which is optionally substituted by a $C_1$- to $C_4$-alkyl radical, by a $C_1$- to $C_4$-hydroxyalkyl radical and/or by a bridge Y or which is optionally part of a bridging ring system,
- the bridge Y is an alkylene group having 1 to 14 carbon atoms, such as, for example, a linear or branched alkylene chain or an alkylene ring which can be terminated or interrupted by one or more nitrogen-containing groups and/or one or more heteroatoms, such as oxygen, sulfur or nitrogen atoms, and may possibly be substituted by one or more hydroxyl or $C_1$- to $C_8$-alkoxy radicals, or a direct bond,
- $G^5$ and $G^6$, independently of one another, are a hydrogen or halogen atom, a $C_1$- to $C_4$-alkyl radical, a $C_1$- to $C_4$-monohydroxyalkyl radical, a $C_2$- to $C_4$-polyhydroxyalkyl radical, a $C_1$- to $C_4$-aminoalkyl radical or a direct bond to the bridge Y,
- $G^7$, $G^8$, $G^9$, $G^{10}$, $G^{11}$ and $G^{12}$, independently of one another, are a hydrogen atom, a direct bond to the bridge Y or a $C_1$- to $C_4$-alkyl radical, with the proviso that the compounds of the formula (E2) contain only one bridge Y per molecule.

According to the invention, the substituents used in formula (E2) are defined analogously to the above statements.

Preferred binuclear developer components of the formula (E2) are in particular: N,N'-bis(β-hydroxyethyl)-N,N'-bis(4'-aminophenyl)-1,3-diaminopropan-2-ol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-diethyl-N,N'-bis(4'-amino-3'-methylphenyl)ethylenediamine, bis(2-hydroxy-5-aminophenyl)methane, N,N'-bis(4'-aminophenyl)-1,4-diazacycloheptane, N,N'-bis(2-hydroxy-5-aminobenzyl)piperazine, N-(4'-aminophenyl)-p-phenylenediamine and 1,10-bis(2',5'-diaminophenyl)-1,4,7,10-tetraoxadecane and their physiologically compatible salts.

Very particularly preferred binuclear developer components of the formula (E2) are N,N'-bis(β-hydroxyethyl)-N,N'-bis(4'-aminophenyl)-1,3-diaminopropan-2-ol, bis(2-hydroxy-5-aminophenyl)methane, 1,3-bis(2,5-diaminophenoxy)propan-2-ol, N,N'-bis(4-aminophenyl)-1,4-diazacycloheptane and 1,10-bis(2,5-diaminophenyl)-1,4,7,10-tetraoxadecane or one of their physiologically compatible salts.

In addition, it may be preferred according to the invention to use a p-aminophenol derivative or one of its physiologically compatible salts as developer component. Particular preference is given to p-aminophenol derivatives of the formula (E3)

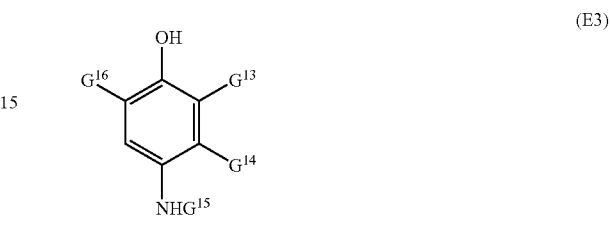

where:
- $G^{13}$ is a hydrogen atom, a halogen atom, a $C_1$- to $C_4$-alkyl radical, a $C_1$- to $C_4$-monohydroxyalkyl radical, a $C_2$- to $C_4$-polyhydroxyalkyl radical, a ($C_1$- to $C_4$)-alkoxy-($C_1$- to $C_4$)-alkyl radical, a $C_1$- to $C_4$-aminoalkyl radical, a hydroxy-($C_1$- to $C_4$)-alkylamino radical, a $C_1$- to $C_4$-hydroxyalkoxy radical, a $C_1$- to $C_4$-hydroxyalkyl-($C_1$- to $C_4$)-aminoalkyl radical or a (di-$C_1$- to $C_4$-alkylamino)-($C_1$- to $C_4$)-alkyl radical, and
- $G^{14}$ is a hydrogen or halogen atom, a $C_1$- to $C_4$-alkyl radical, a $C_1$- to $C_4$-monohydroxyalkyl radical, a $C_2$- to $C_4$-polyhydroxyalkyl radical, a ($C_1$- to $C_4$)-alkoxy-($C_1$- to $C_4$)-alkyl radical, a $C_1$- to $C_4$-aminoalkyl radical or a $C_1$- to $C_4$-cyanoalkyl radical,
- $G^{15}$ is hydrogen, a $C_1$- to $C_4$-alkyl radical, a $C_1$- to $C_4$-monohydroxyalkyl radical, a $C_2$- to $C_4$-polyhydroxyalkyl radical, a phenyl radical or a benzyl radical, and
- $G^{16}$ is hydrogen or a halogen atom.

According to the invention, the substituents used in formula (E3) are defined analogously to the above statements.

Preferred p-aminophenols of the formula (E3) are, in particular, p-aminophenol, N-methyl-p-aminophenol, 4-amino-3-methylphenol, 4-amino-3-fluorophenol, 2-hydroxymethylamino-4-aminophenol, 4-amino-3-hydroxymethylphenol, 4-amino-2-(β-hydroxyethoxy)phenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-(α,β-dihydroxyethyl)phenol, 4-amino-2-fluorophenol, 4-amino-2-chlorophenol, 4-amino-2,6-dichlorophenol, 4-amino-2-(diethylaminomethyl)phenol and their physiologically compatible salts.

Very particularly preferred compounds of the formula (E3) are p-aminophenol, 4-amino-3-methylphenol, 4-amino-2-aminomethylphenol, 4-amino-2-(α,β-dihydroxyethyl)phenol and 4-amino-2-(diethylaminomethyl)phenol.

In addition, the developer component can be chosen from o-aminophenol and its derivatives, such as, for example, 2-amino-4-methylphenol, 2-amino-5-methylphenol or 2-amino-4-chlorophenol.

In addition, the developer component can be chosen from heterocyclic developer components, such as, for example, the pyridine, pyrimidine, pyrazole, pyrazolopyrimidine derivatives and their physiologically compatible salts.

Preferred pyridine derivatives are, in particular, the compounds which are described in the patents GB 1 026 978 and GB 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine.

Preferred pyrimidine derivatives are, in particular, the compounds which are described in the German patent DE 2 359 399, the Japanese laid-open specification JP 02019576 A2 or in the laid-open specification WO 96/15765, such as 2,4,5,6-tetraminopyrimidine, 4-hydroxy-2,5,6-triaminopyrimidine, 2-hydroxy-4,5,6-triaminopyrimidine, 2-dimethylamino-4,5,6-triaminopyrimidine, 2,4-dihydroxy-5,6-diaminopyrimidine and 2,5,6-triaminopyrimidine.

Preferred pyrazole derivatives are, in particular, the compounds which are described in the patents DE 3 843 892, DE 4 133 957 and patent applications WO 94/08969, WO 94/08970, EP-740 931 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(β-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole.

Preferred pyrazolepyrimidine derivatives are, in particular, the derivatives of pyrazole[1,5-a]pyrimidine of the following formula (E4) and its tautomeric forms if a tautomeric equilibrium exists:

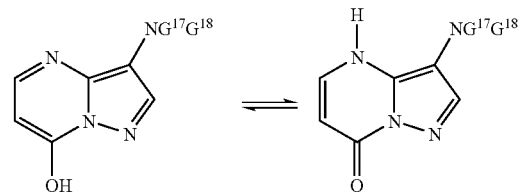

where:
$G^{17}$, $G^{18}$, $G^{19}$ and $G^{20}$, independently of each other, are a hydrogen atom, a $C_1$-$C_4$-alkyl radical, an aryl radical, a $C_1$-$C_4$-hydroxyalkyl radical, a $C_2$-$C_4$-polyhydroxyalkyl radical, a ($C_1$-$C_4$)-alkoxy-($C_1$-$C_4$)-alkyl radical, a $C_1$-$C_4$-aminoalkyl radical, which may be optionally protected by an acetyl ureido or a sulfonyl radical, a ($C_1$-$C_4$)-alkylamino-($C_1$-$C_4$)-alkyl radical, a di[($C_1$-$C_4$)-alkyl]-($C_1$-$C_4$)-aminoalkyl radical, where the dialkyl radicals optionally form a carbon cycle or a heterocycle with 5 or 6 chain members, a $C_1$-$C_4$-hydroxyalkyl radical or a di($C_1$-$C_4$)-[hydroxyalkyl]-($C_1$-$C_4$)-aminoalkyl radical, the X radicals, independently of each other, are a hydrogen atom, a $C_1$-$C_4$-alkyl radical, an aryl radical, a $C_1$-$C_4$-hydroxyalkyl radical, a $C_2$-$C_4$-polyhydroxyalkyl radical, a $C_1$-$C_4$-aminoalkyl radical, a ($C_1$-$C_4$)-alkylamino-($C_1$-$C_4$)-alkyl radical, a di[($C_1$-$C_4$)alkyl]-($C_1$-$C_4$)-aminoalkyl radical, where the dialkyl radicals optionally form a carbon cycle or a heterocycle with 5 or 6 chain members, a $C_1$-$C_4$-hydroxyalkyl or a di($C_1$-$C_4$-hydroxyalkyl)aminoalkyl radical, an amino radical, a $C_1$-$C_4$-alkyl- or di($C_1$-$C_4$-hydroxyalkyl)amino radical, a halogen atom, a carboxylic acid group or a sulfonic acid group, i has the value 0, 1, 2 or 3,
p has the value 0 or 1,
q has the value o or 1 and
n has the value 0 or 1,
with the proviso that
the sum of p+q is not 0,
if p+q is 2, n has the value 0, and the groups $NG^{17}G^{18}$ and $NG^{19}G^{20}$ occupy the positions (2,3); (5,6); (6,7); (3,5) or (3,7);
if p+q is 1, n has the value 1, and the groups $NG^{17}G^{18}$ (or $NG^{19}G^{20}$) and the group OH occupy the positions (2,3); (5,6); (6,7); (3,5) or (3,7);

According to the invention, the substituents used in formula (E4) are defined analogously to the above statements.

If the pyrazolo[1,5-a]pyrimidine of the above formula (E4) contains a hydroxy group at one of positions 2, 5 or 7 of the ring system, a tautomeric equilibrium exists which is represented, for example, in the following scheme:

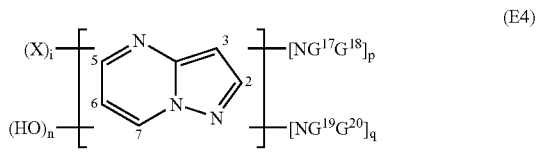

Among the pyrazole[1,5-a]pyrimidines of the above formula (E4) mention may be made in particular of:
pyrazole[1,5-a]pyrimidine-3,7-diamine;
2,5-dimethylpyrazole[1,5-a]pyrimidine-3,7-diamine;
pyrazole[1,5-a]pyrimidine-3,5-diamine;
2,7-dimethylpyrazole[1,5-a]pyrimidine-3,5-diamine;
3-aminopyrazole[1,5-a]pyrimidin-7-ol;
3-aminopyrazole[1,5-a]pyrimidin-5-ol;
2-(3-aminopyrazole[1,5-a]pyrimidin-7-ylamino)ethanol;
2-(7-aminopyrazole[1,5-a]pyrimidin-3-ylamino)ethanol;
2-[(3-aminopyrazole[1,5-a]pyrimidin-7-yl)-(2-hydroxyethyl)amino]ethanol;
2-[(7-aminopyrazole[1,5-a]pyrimidin-3-yl)-(2-hydroxyethyl)amino]ethanol;
5,6-dimethylpyrazole[1,5-a]pyrimidine-3,7-diamine;
2,6-dimethylpyrazole[1,5-a]pyrimidine-3,7-diamine;
3-amino-7-dimethylamino-2,5-dimethylpyrazolo[1,5-a]pyrimidine;

and their physiologically compatible salts and their tautomeric forms if a tautomeric equilibrium is present.

The pyrazole[1,5-a]pyrimidines of the above formula (E4) can be prepared as described in the literature by cyclization starting from an aminopyrazole or from hydrazine.

In a further preferred embodiment, the colorants according to the invention comprise at least one coupler component.

The coupler components used are usually m-phenylenediamine derivatives, naphthols, resorcinol and resorcinol derivatives, pyrazolones and m-aminophenol derivatives.

Suitable coupler substances are, in particular, 1-naphthol, 1,5-, 2,7- and 1,7-dihydroxynaphthalene, 5-amino-2-methylphenol, m-aminophenol, resorcinol, resorcinol monomethyl ether, m-phenylenediamine, 1-phenyl-3-methylpyrazolone-5, 2,4-dichloro-3-aminophenol, 1,3-bis(2',4'-diaminophenoxy)propane, 2-chlororesorcinol, 4-chlororesorcinol, 2-chloro-6-methyl-3-aminophenol, 2-amino-3-hydroxypyridine, 2-methylresorcinol, 5-methylresorcinol and 2-methyl-4-chloro-5-aminophenol.

Coupler components preferred according to the invention are
- m-aminophenol and its derivatives, such as, for example, 5-amino-2-methylphenol, N-cyclopentyl-3-aminophenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2'-hydroxyethyl)amino-2-methylphenol, 3-(diethylamino)phenol, N-cyclopentyl-3-aminophenol, 1,3-dihydroxy-5-(methylamino)benzene, 3-ethylamino-4-methylphenol and 2,4-dichloro-3-aminophenol,
- o-aminophenol and derivatives thereof,
- m-diaminobenzene and derivatives thereof, such as, for example, 2,4-diaminophenoxyethanol, 1,3-bis(2',4'-diaminophenoxy)propane, 1-methoxy-2-amino-4-(2'-hydroxyethylamino)benzene, 1,3-bis(2',4'-diaminophenyl)propane, 2,6-bis(2'-hydroxyethylamino)-1-methylbenzene 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-[3-morpholin-4-ylphenyl)amino]ethanol, 3-amino-4-(2-methoxyethoxy)-5-methylphenylamine and 1-amino-3-bis(2'-hydroxyethyl)aminobenzene,
- o-diaminobenzene and derivatives thereof, such as, for example, 3,4-diaminobenzoic acid and 2,3-diamino-1-methylbenzene,
- di- and trihydroxybenzene derivatives, such as, for example, resorcinol, resorcinol monomethyl ether, 2-methylresorcinol, 5-methylresorcinol, 2,5-dimethylresorcinol, 2-chlororesorcinol, 4-chlororesorcinol, pyrogallol and 1,2,4-trihydroxybenzene,
- pyridine derivatives, such as, for example, 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine and 3,5-diamino-2,6-dimethoxypyridine,
- naphthalene derivatives, such as, for example, 1-naphthol, 2-methyl-1-naphthol, 2-hydroxymethyl-1-naphthol, 2-hydroxyethyl-1-naphthol, 1,5-dihydroxynaphthalene, 1,6-dihydroxynaphthalene, 1,7-dihydroxynaphthalene, 1,8-dihydroxynaphthalene, 2,7-dihydroxynaphthalene and 2,3-dihydroxynaphthalene,
- morpholine derivatives, such as, for example, 6-hydroxybenzomorpholine and 6-aminobenzomorpholine,
- quinoxaline derivatives, such as, for example, 6-methyl-1,2,3,4-tetrahydroquinoxaline,
- pyrazole derivatives, such as, for example, 1-phenyl-3-methylpyrazol-5-one,
- indole derivatives, such as, for example, 4-hydroxyindole, 6-hydroxyindole and 7-hydroxyindole,
- pyrimidine derivatives, such as, for example, 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine, and 4,6-dihydroxy-2-methylpyrimidine, or
- methylenedioxybenzene derivatives, such as, for example, 1-hydroxy-3,4-methylenedioxybenzene, 1-amino-3,4-methylenedioxybenzene and 1-(2-hydroxyethyl)amino-3,4-methylenedioxybenzene, and physiologically compatible salts thereof.

Coupler components which are particularly preferred according to the invention are 1-naphthol, 1,5-, 2,7- and 1,7-dihydroxynaphthalene, 3-aminophenol, 5-amino-2-methylphenol, 2-amino-3-hydroxypyridine, resorcinol, 4-chlororesorcinol, 2-chloro-6-methyl-3-aminophenol, 2-methylresorcinol, 5-methylresorcinol, 2,5-dimethylresorcinol and 2,6-dihydroxy-3,4-dimethylpyridine.

In addition, within the scope of a fifth embodiment, precursors of nature-analogous dyes which can be used in the substances according to the invention are preferably those indoles and indolines which have at least one hydroxy or amino group, preferably as substituent on the six-membered ring. These groups can carry further substituents, e.g. in the form of an etherification or esterification of the hydroxy group or an alkylation of the amino group. In a second preferred embodiment, the colorants comprise at least one indole derivative and/or indoline derivative.

Particularly suitable precursors of nature-analogous hair dyes are derivatives of 5,6-dihydroxyindoline of the formula IIIa,

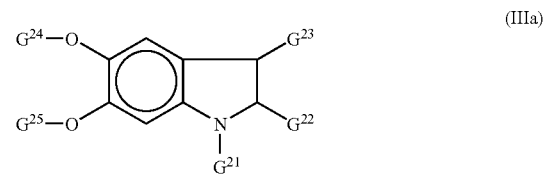

(IIIa)

in which, independently of one another, $G^{21}$ is hydrogen, a $C_1$-$C_4$-alkyl group or a $C_1$-$C_4$-hydroxyalkyl group, $G^{22}$ is hydrogen or a —COOH group, where the —COOH group can also be in the form of a salt with a physiologically compatible cation, $G^{23}$ is hydrogen or a $C_1$-$C_4$-alkyl group, $G^{24}$ is hydrogen, a $C_1$-$C_4$-alkyl group or a group —CO-$G^{26}$, in which $G^{26}$ is a $C_1$-$C_4$-alkyl group, and $G^{25}$ is one of the groups specified under $G^{24}$, and physiologically compatible salts of these compounds with an organic or inorganic acid.

Particularly preferred derivatives of indoline are 5,6-dihydroxyinodoline, N-methyl-5,6-dihydroxyindoline, N-ethyl-5,6-dihydroxyindoline, N-propyl-5,6-dihydroxyindoline, N-butyl-5,6-dihydroxyindoline, 5,6-dihydroxyindoline-2-carboxylic acid, and 6-hydroxyindoline, 6-aminoindoline and 4-aminoindoline.

Within this group, particular emphasis is given to N-methyl-5,6-dihydroxyindoline, N-ethyl-5,6-dihydroxyindoline, N-propyl-5,6-dihydroxyindoline, N-butyl-5,6-dihydroxyindoline and, in particular, 5,6-dihydroxyindoline.

Exceptionally suitable precursors of nature-analogous hair dyes are also derivatives of 5,6-dihydroxyindole of the formula IIIb,

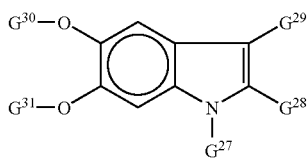

(IIIb)

in which, independently of one another, $G^{27}$ is hydrogen, a $C_1$-$C_4$-alkyl group or a $C_1$-$C_4$-hydroxyalkyl group, $G^{28}$ is hydrogen or a —COOH group, where the —COOH group may also be in the form of a salt with a physiologically compatible cation, $G^{29}$ is hydrogen or a $C_1$-$C_4$-alkyl group, $G^{30}$ is hydrogen, a $C_1$-$C_4$-alkyl group or a group —CO-$G^{32}$, in which $G^{32}$ is a $C_1$-$C_4$-alkyl group, and $G^{31}$ is one of the groups specified under $G^{30}$, and physiologically compatible salts of these compounds with an organic or inorganic acid.

Particularly preferred derivatives of indole are 5,6-dihydroxyindole, N-methyl-5,6-dihydroxyindole, N-ethyl-5,6-dihydroxyindole, N-propyl-5,6-dihydroxyindole, N-butyl-5,6-dihydroxyindole, 5,6-dihydroxyindole-2-carboxylic acid, 6-hydroxyindole, 6-aminoindole and 4-aminoindole.

Within this group, emphasis is placed on N-methyl-5,6-dihydroxyindole, N-ethyl-5,6-dihydroxyindole, N-propyl-5,6-dihydroxyindole, N-butyl-5,6-dihydroxyindole and, in particular, 5,6-dihydroxyindole.

The indoline and indole derivatives can be used in the colorants according to the invention either as free bases or in the form of their physiologically compatible salts with inorganic or organic acids, e.g. the hydrochlorides, sulfates and hydrobromides. The indole derivatives and indoline derivatives are present in these usually in amounts of 0.05-10% by weight, preferably 0.2-5% by weight.

The presence of oxidizing agents, e.g. $H_2O_2$, can be dispensed with, particularly if the substance according to the invention does not comprise oxidation dye precursors. If the substance according to the invention comprises air-oxidizable oxidation dye precursors or indole or indoline derivatives, oxidizing agents can be dispensed with in such a case without problems. However, it may be desirable under certain circumstances to add hydrogen peroxide or other oxidizing agents to the substances according to the invention to achieve nuances which are lighter than the keratinic fibers which are to be colored. Oxidizing agents are generally used in an amount of from 0.01 to 6% by weight, based on the application solution. An oxidizing agent preferred for human hair is $H_2O_2$. Mixtures of two or more oxidizing agents, such as, for example, a combination of hydrogen peroxide and peroxodisulfates of alkali metals and alkaline earth metals or of iodide ion sources, such as, for example, alkali metal iodides and hydrogen peroxide or the abovementioned peroxodisulfates, can also be used. According to the invention, the oxidizing agent or the oxidizing agent combination can be used in combination with oxidation catalysts in the hair colorant. Oxidation catalysts are, for example, metal salts, metal chelate complexes or metal oxides which permit the metal ions to readily alternate between two oxidation states. Examples are salts, chelate complexes or oxides of iron, ruthenium, manganese and copper. Further possible oxidation catalysts are enzymes. Suitable enzymes are, for example, peroxidases, which can considerably enhance the effect of small amounts of hydrogen peroxide. Also suitable according to the invention are those enzymes which directly oxidize the oxidation dye precursors with the help of atmospheric oxygen, such as, for example, the laccases, or in situ produce small amounts of hydrogen peroxide and, in so doing, biocatalytically activate the oxidation of the dye precursors. Particularly suitable catalysts for the oxidation of the dye precursors are the so-called 2-electron oxidoreductases in combination with the substrates specific therefor, e.g.

pyranose oxidase and e.g. D-glucose or galactose, glucose oxidase and D-glucose, glycerol oxidase and glycerol, pyruvate oxidase and pyruvic acid or salts thereof, alcohol oxidase and alcohol (MeOH, EtOH), lactate oxidase and lactic acid and salts thereof, tyrosinase oxidase and tyrosine, uricase and uric acid or salts thereof, choline oxidase and choline, amino acid oxidase and amino acids.

In a sixth embodiment, besides the compounds present according to the invention, the colorants according to the invention additionally comprise, for further modifying the color nuances, customary direct dyes, such as nitrophenylenediamines, nitroaminophenols, azo dyes, anthraquinones or indophenols. Preferred direct dyes are the compounds known under the international names or trade names HC Yellow 2, HC Yellow 4, HC Yellow 5, HC Yellow 6, HC Yellow 12, Acid Yellow 1, Acid Yellow 10, Acid Yellow 23, Acid Yellow 36, HC Orange 1, Disperse Orange 3, Acid Orange 7, HC Red 1, HC Red 3, HC Red 10, HC Red 11, HC Red 13, Acid Red 33, Acid Red 52, HC Red BN, Pigment Red 57:1, HC Blue 2, HC Blue 12, Disperse Blue 3, Acid Blue 7, Acid Green 50, HC Violet 1, Disperse Violet 1, Disperse Violet 4, Acid Violet 43, Disperse Black 9, Acid Black 1, and Acid Black 52, and 1,4-diamino-2-nitrobenzene, 2-amino-4-nitrophenol, 1,4-bis(β-hydroxyethyl)amino-2-nitrobenzene, 3-nitro-4-(β-hydroxyethyl)aminophenol, 2-(2'-hydroxyethyl)amino-4,6-dinitrophenol, 1-(2'-hydroxyethyl)amino-4-methyl-2-nitrobenzene, 1-amino-4-(2'-hydroxyethyl)amino-5-chloro-2-nitrobenzene, 4-amino-3-nitrophenol, 1-(2'-ureidoethyl)amino-4-nitrobenzene, 4-amino-2-nitrodiphenylamine-2'-carboxylic acid, 6-nitro-1,2,3,4-tetrahydroquinoxaline, 2-hydroxy-1,4-naphthoquinone, picraminic acid and salts thereof, 2-amino-6-chloro-4-nitrophenol, 4-ethylamino-3-nitrobenzoic acid and 2-chloro-6-ethylamino-1-hydroxy-4-nitrobenzene.

In addition, the substances according to the invention can preferably comprise a cationic direct dye. Particular preference is given here to (a) cationic triphenylmethane dyes, such as, for example, Basic Blue 7, Basic Blue 26, Basic Violet 2 and Basic Violet 14, (b) aromatic systems which are substituted by a quaternary nitrogen group, such as, for example, Basic Yellow 57, Basic Red 76, Basic Blue 99, Basic Brown 16 and Basic Brown 17, and (c) direct dyes which contain a heterocycle which has at least one quaternary nitrogen atom, as are specified, for example, in EP-A2-998 908, to which reference is explicitly made at this point, in claims 6 to 11.

Preferred cationic direct dyes of group (c) are, in particular, the following compounds:

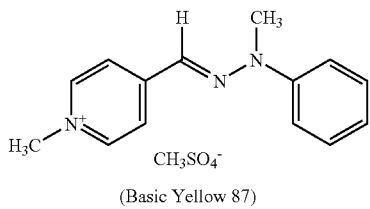
(DZ1) (Basic Yellow 87)

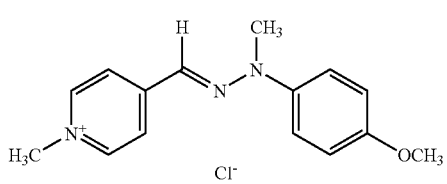
(DZ2)

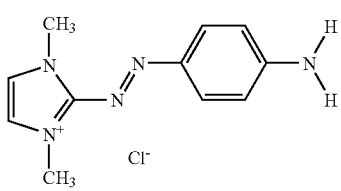
(DZ3) (Basic Orange 31)

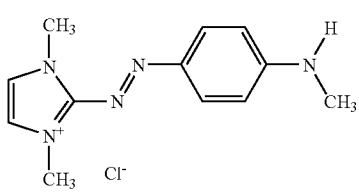
(DZ4)

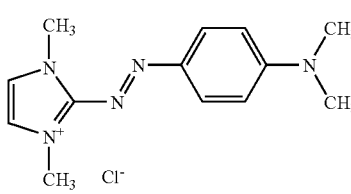
(DZ5) (Basic Red 51)

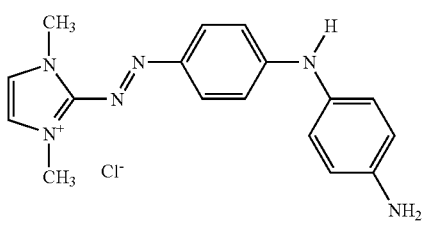
(DZ6)

(DZ7)

-continued

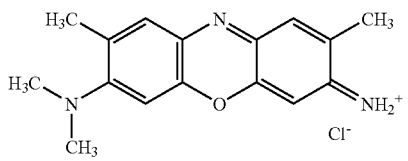
(DZ8)

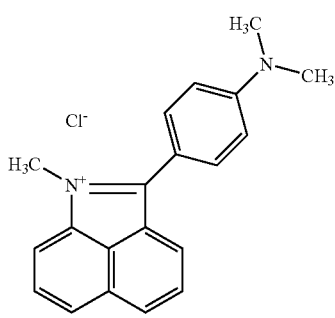
(DZ9)

The Compounds of the Formulae (DZ1), (DZ3) and (DZ5) are very particularly preferred cationic direct dyes of group (c). The cationic direct dyes which are sold under the trade name Arianor® are particularly preferred direct dyes according to the invention.

The substances according to the invention in accordance with this embodiment comprise the direct dyes preferably in an amount of from 0.01 to 20% by weight, based on the total colorant.

In addition, the preparations according to the invention can also comprise naturally occurring dyes, such as, for example, henna red, henna neutral, henna black, camomile blossom, sandalwood, black tea, buckthorn bark, sage, logwood, madder root, catechu, sedre and alkanna root.

It is not necessary for the optionally present direct dyes to each constitute uniform compounds. Instead, as a result of the preparation processes for the individual dyes, it is also possible for further components to be present in the colorants according to the invention in secondary amounts provided these do not adversely affect the coloring result or have to be excluded for other reasons, e.g. toxicological reasons.

To achieve further and more intense colorations, the substances according to the invention can additionally comprise color enhancers. The color enhancers are preferably chosen from the group consisting of piperidine, piperidine-2-carboxylic acid, piperidine-3-carboxylic acid, piperidine-4-carboxylic acid, pyridine, 2-hydroxypyridine, 3-hydroxypyridine, 4-hydroxypyridine, imidazole, 1-methylimidazole, arginine, histidine, pyrrolidine, proline, pyrrolidone, pyrrolidone-5-carboxylic acid, pyrazole, 1,2,4-triazole, piperazidine, derivatives thereof, and physiologically compatible salts thereof.

The abovementioned color enhancers may be used in an amount of in each case 0.03 to 65 mmol, in particular 1 to 40 mmol, in each case based on 100 g of the total colorant.

The colorants according to the invention produce intense colorations even at physiologically compatible temperatures of below 45° C. They are therefore particularly suitable for dyeing human hair. For use on human hair, the colorants can usually be incorporated into a hydrous cosmetic carrier. Suitable hydrous cosmetic carriers are, for example, creams, emulsions, gels, or surfactant-containing foaming solutions, such as, for example, shampoos or other preparations which are suitable for application to the keratinic fibers. If required, it is also possible to incorporate the colorants into anhydrous carriers.

In addition, the colorants according to the invention can comprise all active ingredients, additives and auxiliaries known in such preparations. In many cases, the colorants comprise at least one surfactant, with both anionic and also zwitterionic, ampholytic, nonionic and cationic surfactants being suitable in principle. In many cases, it has, however, proven to be advantageous to choose the surfactants from anionic, zwitterionic or nonionic surfactants.

Suitable anionic surfactants in preparations according to the invention are all anionic surface-active substances suitable for use on the human body. These are characterized by a water-solubilizing, anionic group, such as, for example, a carboxylate, sulfate, sulfonate or phosphate group, and a lipophilic alkyl group having about 10 to 22 carbon atoms. In addition, glycol or polyglycol ether groups, ester groups, ether groups and amide groups and also hydroxyl groups, may be present in the molecule. Examples of suitable anionic surfactants are, in each case in the form of the sodium, potassium and ammonium and also the mono-, di- and trialkanolammonium salts having 2 or 3 carbon atoms in the alkanol group,

- linear fatty acids having 10 to 22 carbon atoms (soaps),
- ether carboxylic acids of the formula R—O—(CH$_2$—CH$_2$O)$_x$—CH$_2$—COOH, in which R is a linear alkyl group having 10 to 22 carbon atoms and x=0 or 1 to 16,
- acyl sarcosides having 10 to 18 carbon atoms in the acyl group,
- acyl taurides having 10 to 18 carbon atoms in the acyl group,
- acyl isethionates having 10 to 18 carbon atoms in the acyl group,
- sulfosuccinic mono- and dialkyl esters having 8 to 18 carbon atoms in the alkyl group and sulfosuccinic monoalkylpolyoxyethyl esters having 8 to 18 carbon atoms in the alkyl group and 1 to 6 oxyethyl groups,
- linear alkanesulfonates having 12 to 18 carbon atoms,
- linear alpha-olefin sulfonates having 12 to 18 carbon atoms,
- alpha-sulfo fatty acid methyl esters of fatty acids having 12 to 18 carbon atoms,
- alkyl sulfates and alkyl polyglycol ether sulfates of the formula R—O(CH$_2$—CH$_2$O)$_x$—SO$_3$H, in which R is a preferably linear alkyl group having 10 to 18 carbon atoms and x=0 or 1 to 12,
- mixtures of surface-active hydroxysulfonates according to DE-A-37 25 030,
- sulfated hydroxyalkyl polyethylene and/or hydroxyalkylene propylene glycol ethers according to DE-A-37 23 354,
- sulfonates of unsaturated fatty acids having 12 to 24 carbon atoms and 1 to 6 double bonds according to DE-A-39 26 344,
- esters of tartaric acid and citric acid with alcohols, which constitute addition products of about 2 to 15 molecules of ethylene oxide and/or propylene oxide onto fatty alcohols having 8 to 22 carbon atoms.

Preferred anionic surfactants are alkyl sulfates, alkyl polyglycol ether sulfates and ether carboxylic acids having 10 to 18 carbon atoms in the alkyl group and up to 12 glycol ether groups in the molecule, and in particular salts of saturated and in particular unsaturated $C_8$-$C_{22}$-carboxylic acids, such as oleic acid, stearic acid, isostearic acid and palmitic acid.

Zwitterionic surfactants is the term used to refer to those surface-active compounds which carry at least one quaternary ammonium group and at least one —COO$^{(-)}$ or —SO$_3^{(-)}$ group in the molecule. Particularly suitable zwitterionic surfactants are the so-called betaines, such as the N-alkyl-N,N-dimethylammonium glycinates, for example cocoalkyl dimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazolines having in each case 8 to 18 carbon atoms in the alkyl or acyl group, and cocoacylaminoethyl hydroxyethylcarboxymethyl glycinate. A preferred zwitterionic surfactant is the fatty acid amide derivative known under the CTFA name Cocamidopropyl Betaine.

Ampholytic surfactants are understood as meaning those surface-active compounds which, apart from a $C_{8-18}$-alkyl or -acyl group in the molecule, contain at least one free amino group and at least one —COOH or —SO$_3$H group and are capable of forming internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids having in each case about 8 to 18 carbon atoms in the alkyl group. Particularly preferred ampholytic surfactants are N-cocoalkylaminopropionate, cocoacylaminoethylaminopropionate and $C_{12-18}$-acylsarcosine.

Nonionic surfactants contain, as hydrophilic group, e.g. a polyol group, a polyalkylene glycol ether group or a combination of polyol and polyglycol ether group. Such compounds are, for example,

- addition products of from 2 to 30 mol of ethylene oxide and/or 0 to 5 mol of propylene oxide onto linear fatty alcohols having 8 to 22 carbon atoms, onto fatty acids having 12 to 22 carbon atoms and onto alkylphenols having 8 to 15 carbon atoms in the alkyl group,
- $C_{12-22}$ fatty acid mono- and diesters of addition products of from 1 to 30 mol of ethylene oxide onto glycerol,
- $C_{8-22}$-alkyl mono- and oligoglycosides and ethoxylated analogs thereof,
- addition products of from 5 to 60 mol of ethylene oxide onto castor oil and hydrogenated castor oil,
- addition products of ethylene oxide onto sorbitan fatty acid esters
- addition products of ethylene oxide onto fatty acid alkanolamides.

Examples of the cationic surfactants which can be used in the hair-treatment substances according to the invention are, in particular, quaternary ammonium compounds. Preference is given to ammonium halides, such as alkyltrimethylammonium chlorides, dialkyldimethylammonium chlorides, and trialkylmethylammonium chlorides, e.g. cetyltrimethylammonium chloride, stearyltrimethylammonium chloride, distearyldimethylammonium chloride, lauryidimethylammonium chloride, lauryldimethylbenzylammonium chloride and tricetylmethylammonium chloride. Further cationic surfactants which can be used according to the invention are the quaternized protein hydrolysates.

Likewise suitable according to the invention are cationic silicone oils, such as, for example, the commercially available products Q2-7224 (manufacturer: Dow Corning; a stabilized trimethylsilylamodimethicone), Dow Corning 929 Emulsion (comprising a hydroxylamino-modified silicone, which is also referred to as amodimethicone), SM-2059 (manufacturer: General Electric), SLM-55067 (manufacturer:

Wacker), and Abil®-Quat 3270 and 3272 (manufacturer: Th. Goldschmidt; diquaternary polydimethylsiloxanes, quaternium-80).

Alkylamidoamines, in particular fatty acid amidoamines, such as the stearylamidopropyldimethylamine obtainable under the name Tego Amid®S 18, are characterized not only by a good conditioning effect but specifically by their good biodegradability.

Likewise of very good biodegradability are quaternary ester compounds, so-called "ester quats", such as the methylhydroxyalkyldialkoyloxyalkylammonium methosulfates sold under the trade name Stepantex®.

One example of a quaternary sugar derivative which can be used as cationic surfactant is the commercial product Glucquat® 100, according to CTFA nomenclature a "Lauryl Methyl Gluceth-10 Hydroxypropyl Dimonium Chloride".

The compounds with alkyl groups used as surfactants may in each case be uniform substances. However, it is usually preferred, when manufacturing these substances, to start from native vegetable or animal raw materials, thus giving rise to mixtures of substances with different alkyl chain lengths which depend on the particular raw material.

In the case of surfactants which constitute addition products of ethylene oxide and/or propylene oxide onto fatty alcohols or derivatives of these addition products, it is possible to use either products with a "normal" homolog distribution or those with a narrowed homolog distribution. In this connection, "normal" homolog distribution is understood as meaning mixtures of homologs which are obtained during the reaction of fatty alcohol and alkylene oxide using alkali metals, alkali metal hydroxides or alkali metal alkoxides as catalysts. Narrowed homolog distributions are, by contrast, obtained if, for example, hydrotalcites, alkaline earth metal salts of ether carboxylic acids, alkaline earth metal oxides, hydroxides or alkoxides are used as catalysts. The use of products with a narrowed homolog distribution may be preferred.

Further active ingredients, auxiliaries and additives are, for example, nonionic polymers, such as, for example, vinylpyrrolidone/vinyl acrylate copolymers, polyvinylpyrrolidone and vinylpyrrolidone/vinyl acetate copolymers and polysiloxanes, cationic polymers, such as quaternized cellulose ethers, polysiloxanes with quaternary groups, dimethyldiallylammonium chloride polymers, acrylamide-dimethyldiallylammonium chloride copolymers, dimethylaminoethyl methacrylate-vinylpyrrolidone copolymers quaternized with diethyl sulfate, vinylpyrrolidone-imidazolinium methochloride copolymers and quaternized polyvinyl alcohol, zwitterionic and amphoteric polymers, such as, for example, acrylamidopropyltrimethylammonium chloride/acrylate copolymers and octylacrylamide/methyl methacrylate/tert-butylaminoethyl methacrylate/2-hydroxypropyl methacrylate copolymers, anionic polymers, such as, for example, polyacrylic acids, crosslinked polyacrylic acids, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and acrylic acid/ethyl acrylate/N-tert-butylacrylamide terpolymers, thickeners, such as agar-agar, guar gum, alginates, xanthan gum, gum arabic, karaya gum, carob seed flour, linseed gums, dextrans, cellulose derivatives, e.g. methylcellulose, hydroxyalkylcellulose and carboxymethylcellulose, starch fractions and derivatives, such as amylose, amylopectin and dextrins, clays, such as, for example, bentonite or completely synthetic hydrocolloids, such as, for example, polyvinyl alcohol, structurants, such as glucose and maleic acid, hair-conditioning compounds, such as phospholipids, for example soya lecithin, egg lecithin and cephalins, and silicone oils, protein hydrolysates, in particular elastin, collagen, keratin, milk protein, soya protein and wheat protein hydrolysates, condensation products thereof with fatty acids, and quaternized protein hydrolysates, perfume oils, dimethyl isosorbide and cyclodextrins, solubility promoters, such as ethanol, isopropanol, ethylene glycol, propylene glycol, glycerol and diethylene glycol, antidandruff active ingredients, such as piroctone olamine and zinc omadine, further substances for adjusting the pH, active ingredients, such as panthenol, pantothenoic acid, allantoin, pyrrolidonecarboxylic acids and salts thereof, plant extracts and vitamins, cholesterol, photoprotective agents, consistency regulators, such as sugar esters, polyol esters or polyol alkyl ethers, fats and waxes, such as spermaceti, beeswax, montan wax, paraffins, fatty alcohols and fatty acid esters, fatty acid alkanolamides, complexing agents, such as EDTA, NTA and phosphonic acids, swelling and penetration substances, such as glycerol, propylene glycol monoethyl ether, carbonates, hydrogencarbonates, guanidines, ureas, and primary, secondary and tertiary phosphates, imidazoles, tannins, pyrrole, opacifiers, such as latex, pearlizing agents, such as ethylene glycol mono- and distearate, propellants, such as propane/butane mixtures, $N_2O$, dimethyl ether, $CO_2$ and air, and antioxidants.

The constituents of the hydrous carrier are used for producing the colorants according to the invention in amounts customary for this purpose; e.g. emulsifiers are used in concentrations of from 0.5 to 30% by weight and thickeners are used in concentrations of from 0.1 to 25% by weight, of the total colorant.

For the coloring result, it may be advantageous to add ammonium or metal salts to the colorants. Suitable metal salts are, for example, formiates, carbonates, halides, sulfates, butyrates, valeriates, capronates, acetates, lactates, glycolates, tartrates, citrates, gluconates, propionates, phosphates and phosphonates of alkali metals, such as potassium, sodium or lithium, alkaline earth metals, such as magnesium, calcium, strontium or barium, or of aluminum, manganese, iron, cobalt, copper or zinc, where sodium acetate, lithium bromide, calcium bromide, calcium gluconate, zinc chloride, zinc sulfate, magnesium chloride, magnesium sulfate, ammonium carbonate, ammonium chloride and ammonium acetate are preferred. These salts are preferably present in an amount of from 0.03 to 65 mmol, in particular from 1 to 40 mmol, based on 100 g of the total colorant.

The pH of the ready-to-use coloring preparations is usually between 2 and 11, preferably between 5 and 10.

The present invention secondly provides the use of at least one compound according to formula I and/or its enamine form,

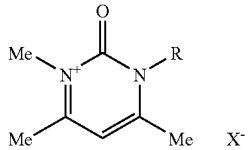

where
R is an allyl group, a hydroxy-($C_2$- to $C_6$)-alkyl group or an optionally substituted benzyl group,
$X^-$ is a physiologically compatible anion together with at least one aldehyde as component B chosen from the group consisting of 4-hydroxy-3-methoxybenzaldehyde, 3,5-dimethoxy-4-hydroxybenzaldehyde, 4-hydroxy-1-naphthaldehyde, 4-hydroxy-2-methoxybenzaldehyde, 3,4-dihydroxy-5-methoxybenzaldehyde, 3,4,5-trihydroxybenzaldehyde, 3,5-dibromo-4-hydroxybenzaldehyde, 4-hydroxy-3-nitrobenzaldehyde, 3-bromo-4-hydroxybenzaldehyde, 4-hydroxy-3-methylbenzaldehyde, 3,5-dimethyl-4-hydroxybenzaldehyde, 5-bromo-4-hydroxy-3-methoxybenzaldehyde, 4-diethylamino-2-hydroxybenzaldehyde and 4-dimethylamino-2-methoxybenzaldehyde, as dyeing component in hair colorants.

In one preferred embodiment, use is made of those compounds according to formula I as dyeing component in hair colorants which are chosen from the preferred and particularly preferred representatives named in the first subject matter of the invention.

Moreover, it may be preferred to use at least one reaction product RP of a compound according to formula I and a representative of component B as dyeing components in hair colorants.

A third subject matter of the present invention relates to a method of dyeing keratinic fibers, in particular human hair, in which a colorant comprising at least one compound according to formula I and/or its enamine form,

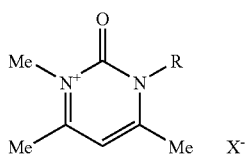

where
R is an allyl group, a hydroxy-($C_2$- to $C_6$)-alkyl group or an optionally substituted benzyl group,
$X^-$ is a physiologically compatible anion together with at least one aldehyde as component B chosen from the group consisting of 4-hydroxy-3-methoxybenzaldehyde, 3,5-dimethoxy-4-hydroxybenzaldehyde, 4-hydroxy-1-naphthaldehyde, 4-hydroxy-2-methoxybenzaldehyde, 3,4-dihydroxy-5-methoxybenzaldehyde, 3,4,5-trihydroxybenzaldehyde, 3,5-dibromo-4-hydroxybenzaldehyde, 4-hydroxy-3-nitrobenzaldehyde, 3-bromo-4-hydroxybenzaldehyde, 4-hydroxy-3-methylbenzaldehyde, 3,5-dimethyl-4-hydroxybenzaldehyde, 5-bromo-4-hydroxy-3-methoxybenzaldehyde, 4-diethylamino-2-hydroxybenzaldehyde and 4-dimethylamino-2-methoxybenzaldehyde, and customary cosmetic ingredients, is applied to the keratinic fibers, left on the fibers for a certain time, usually about 15-30 minutes, and is then rinsed out again or washed out with a shampoo. During the contact time of the agent on the fibers, it may be advantageous to assist the coloring process by introducing heat. Heat can be introduced through an external heat source, such as, for example, warm air from a hot-air fan, or, particularly in the case of hair coloration on a living subject, through the body temperature of the subject. In the case of the latter option, the area to be colored is usually covered with a cap.

Here, the compounds according to formula I and the compounds of component B, especially their preferred and particularly preferred representatives specified above, can be applied to the hair as color-imparting components either simultaneously or successively, i.e. in a multistage process, in which case it is unimportant which of the components is applied first. The optionally present ammonium or metal salts can here be added to the compounds with the formula I or the compounds of component B. There may be an interval of up to 30 minutes between the application of the individual components. A pretreatment of the fibers with the salt solution is also possible.

Prior to using the substance according to the invention in the method according to the invention, it may be desirable to subject the keratinic fibers to be colored to a pretreatment. The order of the pretreatment step required for this and the application of the substance according to the invention does not have to be directly successive, there may instead be a period of up to at most two weeks between the pretreatment step and the application of the substance according to the invention. Several pretreatment methods are suitable for this purpose. Preferably, the fiber is subjected P1 to bleaching before applying the substance according to the invention or P2 to oxidative coloring before applying the substance according to the invention.

In the course of the pretreatment P1, the fiber containing keratin is treated with a bleaching agent. Besides an oxidizing agent, such as customarily hydrogen peroxide, the bleaching agent preferably comprises at least one inorganic persalt which acts as oxidation and bleaching enhancer, such as, for example, a peroxodisulfate of sodium, potassium or ammonium. Colorations according to the method according to the invention through the pretreatment P1 are given a particular brilliance and depth of color.

In the course of the pretreatment P2, an agent comprising the abovementioned oxidation dye precursors as developer component and optionally coupler component, and optionally the abovementioned derivatives of indole and/or indoline is applied to the fiber and, after a contact time, optionally with the addition of the abovementioned suitable oxidizing agents to the hair, is left for 5-45 minutes on the keratin fiber. The hair is then rinsed. By subsequently applying the substance according to the invention, a new color nuance can be imparted to existing oxidation colorations. If the color nuance of the substance according to the invention chosen is the same color nuance of the oxidative coloration, then the coloration of existing oxidation colorations can be freshened up by the method according to the invention. It has been found that freshening up the color or nuancing according to the method according to the invention for freshening up the color or nuancing is on its own superior to conventional direct dyes in terms of the color brilliance and depth of color.

If, besides the compounds according to formula I and the compounds of component B, the hair colorant additionally comprises, as oxidizing agent, hydrogen peroxide or an oxidizing agent mixture containing hydrogen peroxide, then the pH of the hair colorant containing hydrogen peroxide is preferably in a pH range from pH 7 to pH 11, particularly preferably pH 8 to pH 10. The oxidizing agent can be mixed with the hair colorant directly prior to use and the mixture applied to the hair. If the compounds of the formula I and component B are applied in a two-stage method to the hair, the oxidizing agent is to be applied in one of the two process stages together with the corresponding color-imparting component. For this purpose, it may be preferred to formulate the oxidizing agent with one of the color-imparting components in a container.

The compounds according to formula I and the compounds of component B can either be stored separately or together, either in a liquid to pasty preparation (hydrous or anhydrous) or as dry powder. If the components are stored together in a liquid preparation, then this should be largely anhydrous to lessen a reaction of the components. In the case of separate storage, the reactive components are only mixed together intimately directly prior to application. In the case of dry storage, prior to application, a defined amount of warm (30° C. to 80° C.) water is usually added and a homogenous mixture is prepared.

A fourth subject matter of the invention is the use of at least one compound according to formula I and/or its enamine form,

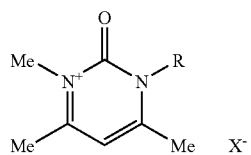
(I)

where

R is an allyl group, a hydroxy-($C_2$- to $C_6$)-alkyl group or an optionally substituted benzyl group, $X^-$ is a physiologically compatible anion together with at least one aldehyde as component B chosen from the group consisting of 4-hydroxy-3-methoxybenzaldehyde, 3,5-dimethoxy-4-hydroxybenzaldehyde, 4-hydroxy-1-naphthaldehyde, 4-hydroxy-2-methoxybenzaldehyde, 3,4-dihydroxy-5-methoxybenzaldehyde, 3,4,5-trihydroxybenzaldehyde, 3,5-dibromo-4-hydroxybenzaldehyde, 4-hydroxy-3-nitrobenzaldehyde, 3-bromo-4-hydroxybenzaldehyde, 4-hydroxy-3-methylbenzaldehyde, 3,5-dimethyl-4-hydroxybenzaldehyde, 5-bromo-4-hydroxy-3-methoxybenzaldehyde, 4-diethylamino-2-hydroxybenzaldehyde and 4-dimethylamino-2-methoxybenzaldehyde, for the nuancing of oxidation colorations of keratinic fibers, in particular human hair. During use, it is unimportant whether the nuancing takes place at the same time during the oxidative coloration, or the oxidative coloration precedes the nuancing.

A fifth subject matter of the invention is the use of at least one compound according to formula I and/or its enamine form,

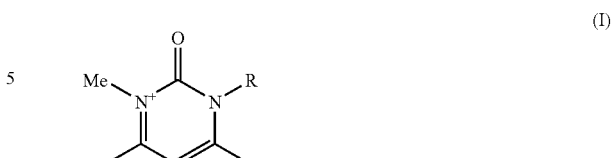
(I)

where

R is an allyl group, a hydroxy-($C_2$- to $C_6$)-alkyl group or an optionally substituted benzyl group, $X^-$ is a physiologically compatible anion together with at least one aldehyde as component B chosen from the group consisting of 4-hydroxy-3-methoxybenzaldehyde, 3,5-dimethoxy-4-hydroxybenzaldehyde, 4-hydroxy-1-naphthaldehyde, 4-hydroxy-2-methoxybenzaldehyde, 3,4-dihydroxy-5-methoxybenzaldehyde, 3,4,5-trihydroxybenzaldehyde, 3,5-dibromo-4-hydroxybenzaldehyde, 4-hydroxy-3-nitrobenzaldehyde, 3-bromo-4-hydroxybenzaldehyde, 4-hydroxy-3-methylbenzaldehyde, 3,5-dimethyl-4-hydroxybenzaldehyde, 5-bromo-4-hydroxy-3-methoxybenzaldehyde, 4-diethylamino-2-hydroxybenzaldehyde and 4-dimethylamino-2-methoxybenzaldehyde, for freshening up the color of keratinic fibers dyed using oxidative colorants.

As is known, the colorations of keratinic fibers are exposed to environmental influences, such as, for example, light, rubbing or washes and can, as a result, lose brilliance and color depth. In the worst case scenario, a nuance shift in the coloration may occur. Such aged colorations of keratinic fibers can, if the user desires, be converted again almost to the colored state as presented itself directly after the original coloration by freshening up the color. It is in accordance with the invention to use a combination of at least one compound with the formula I and at least one compound of component B for such a freshening up of color.

A sixth subject matter of the invention is compounds according to formula I,

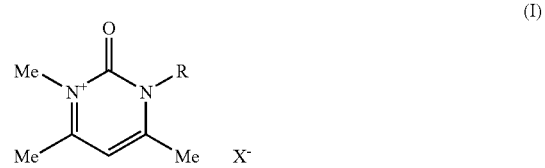
(I)

where

R is an allyl group, a hydroxy-($C_2$- to $C_6$)-alkyl group or an optionally substituted benzyl group and $X^-$ is a physiologically compatible anion.

Preferred and particularly preferred representatives for R and $X^-$ according to formula (I) are the representatives of the first subject matter of the invention.

Particular preference is given to the compounds of the formulae (II-1) to (II-12)

(II-1) 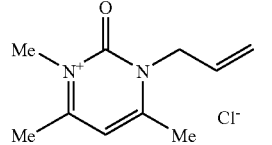

(II-2) 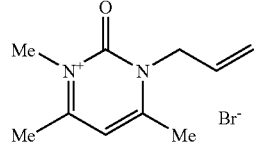

(II-3) 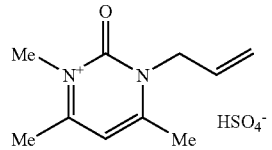

(II-4) 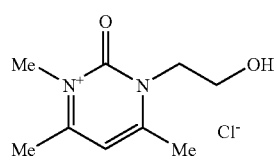

(II-5) 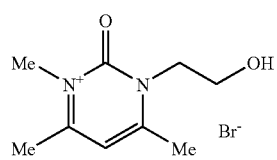

(II-6) 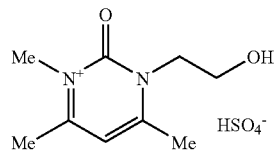

(II-7) 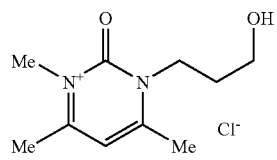

(II-8) 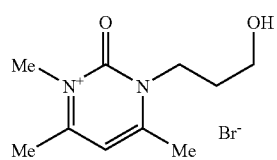

(II-9) 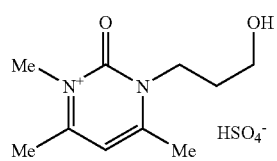

(II-10) 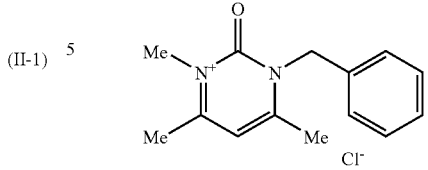

(II-11) 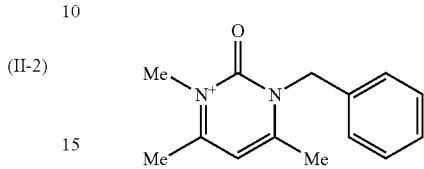

(II-12) 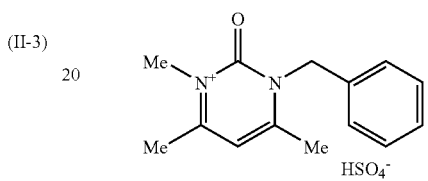

EXAMPLES

1.0 Synthesis of 1,2-dihydro-3,4,6-trimethyl-2-oxopyrimidinium derivatives

Synthesis Example 1

1.1.1 Synthesis of 1,4,6-trimethylpyrimidin-2(1H)-one 20.0 g (0.262 mol) of N-methylurea and 29.4 g (0.291 mol) of acetylacetone were together dissolved in 100 ml of absolute ethanol. 97 g of concentrated sulfuric acid were then added, and the reaction mixture heated up. The mixture was then after-stirred for 1 hour at room temperature. After just a short time, the hydrogen sulfate salt of the product precipitated out in the form of a pale, crystalline solid, which was filtered off. This salt was dissolved in a small amount of water and the solution was rendered neutral using 10% strength sodium hydroxide solution. Extraction was then carried out by shaking with chloroform, and the solvent was dried with magnesium sulfate. After removing the solvent on a rotary evaporator, the desired product was produced in the form of pale pink-colored crystals.

M.p.: 58-60° C. (Lit.: 63° C.; William J. Hale; *J. Am. Chem. Soc.* 1914, 36, 104-115)

Yield: 23.6 g (65.2%)

$^1$H NMR (400 MHz, DMSO-d$_6$): δ [ppm]=2.19 (s, 3H); 2.30 (s, 3H); 3.38 (s, 3H); 6.24 (s, 1H)

1.1.2 Synthesis of 1-allyl-1,2-dihydro-3,4,6-trimethyl-2-oxopyrimidinium bromide A mixture of 8.0 g (0.058 mol) of 1,4,6-trimethylpyrimidin-2(1H)-one and 14.0 g (0.116 mol) of allyl bromide were heated together under reflux in acetonitrile for 16 hours under an inert gas atmosphere. After cooling, a violet solid precipitated out, which was filtered off with suction. The product was purified by recrystallization from chloroform/diethyl ether.

M.p.: 187-191° C.
Yield: 11.7 g (77.8%)
$^1$H NMR (400 MHz, DMSO-$d_6$): δ [ppm]=2.63 (s, 3H); 2.69 (s, 3H); 3.67 (s, 3H); 4.75 (d, 2H); 5.72-5.80 (2×dd, 2H); 5.85-6.01 (m, 1H); 7.09 (s, 1H)

Synthesis Example 2

1.2.1 Synthesis Analogous to the First Stage in Synthesis Example 1 Under 1.1.1

1.2.2 Synthesis of 1,2-dihydro-1-(3-hydroxypropyl)-3,4,6-trimethyl-2-oxopyrimidinium bromide A mixture of 10.0 g (0.072 mol) of 1,4,6-trimethylpyrimidin-2(1H)-one and 20.6 g (0.144 mol) of 3-bromopropanol was heated under reflux in acetonitrile for 16 hours under an inert gas atmosphere. After cooling, a pale pink-colored solid precipitated out, which was filtered off with suction (starting material). The filtrate was admixed with chloroform, then the same amount of diethyl ether was added. The product separated out in the form of an oil.
Yield: 15.4 g (77.4%)
$^1$H NMR (400 MHz, DMSO-$d_6$): δ [ppm]=1.72-1.86 (m, 2H); 2.53 (s, 3H); 2.73 (s, 3H); 3.47 (t, 2H); 3.65 (s, 3H); 4.18 (t, 2H); 7.11 (s, 1H)

Synthesis Example 3

3.1.1 Synthesis of 4,6-dimethyl-1-(2-hydroxyethyl)pyrimidin-2(1H)one

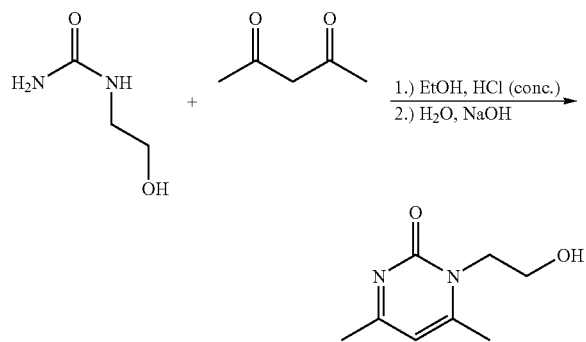

13 g of concentrated hydrochloric acid were added dropwise to a mixture of 10.0 g (0.091 mol) of 2-(hydroxyethyl) urea and 36.9 g (0.365 mol) of acetylacetone in 140 ml of ethanol. When the dropwise addition was complete, the reaction mixture was heated at 70° C. for 9 hours. After about 1.5 hours, the formerly clear reaction solution became cloudy, and the desired product began to precipitate out in the form of its hydrochloride salt. After cooling the reaction mixture, the solid was filtered off and dissolved in water. Dilute sodium hydroxide solution was added to establish a pH of 6-7, the water was removed on a rotary evaporator under reduced pressure and the residue was taken up in acetonitrile. Separation from the remaining solid (NaCl) by filtration was carried out and the organic phase was freed again from the solvent on a rotary evaporator. The product was produced in the form of a white powder.
M.p.: 138-140° C. (Lit.: 139-141° C.; V. S. Reznik et al.; *Pharmaceutical Chemistry Journal* (*Translation of Khimiko-Farmatsevticheskii Zhurnal*), 2001, 35(12), 672-676)

Yield: 10.7 g (69%)
$^1$H NMR (400 MHz, DMSO-$d_6$): δ [ppm]=2.21 (s, 3H); 2.43 (s, 3H); 3.62 (t, 2H); 3.97 (t, 2H); 6.36 (s, 1H)

3.1.2 Synthesis of 1,2-dihydro-1-(2-hydroxyethyl)-3,4,6-trimethyl-2-oxopyrimidinium p-toluenesulfonate

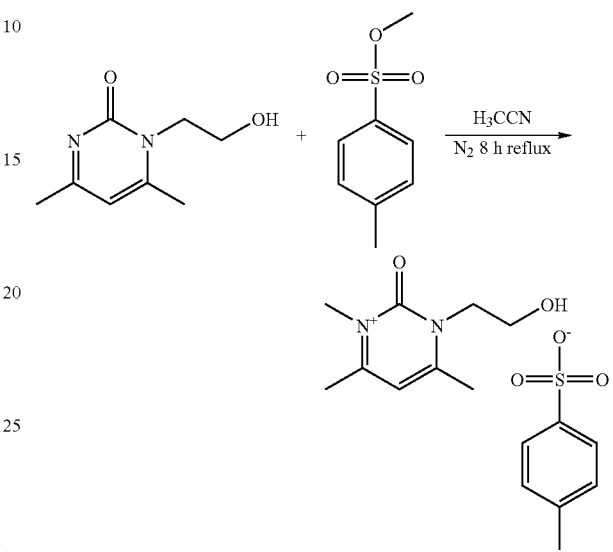

Under a protective-gas atmosphere, a mixture of 9.2 g (0.055 mol) of 4,6-dimethyl-1-(2-hydroxyethyl)pyrimidin-2 (1H)-one and 13.1 g (0.068 mol) of methyl p-toluenesulfonate in 700 ml of acetonitrile was heated under reflux for 12 hours. After cooling, about ⅔ of the solvent was removed on a rotary evaporator, the remaining residue was mixed with the same amount of diethyl ether and cooled to 0° C. At low temperature, firstly an oil separated off, which crystallized out after some time. The crystalline product was filtered off.
M.p.: 110-115° C.
Yield: 17.1 g (88%)
$^1$H NMR (400 MHz, DMSO-$d_6$): δ [ppm]=2.26 (s, 3H); 2.62 (s, 3H); 2.74 (s, 3H); 3.67 (s, 3H); 3.77 (t, 2H); 4.19 (t, 3H); 7.03 (s, 1H); 7.12 (d, 2H) 7.47 (d, 2H)

2.0 Preparation of the Colorants

Aqueous gel formulation for component A Gel 1:

| | |
|---|---|
| CH-acidic compound (component A) | 10 mmol |
| Natrosol HR 250 | 2 g |
| Water, demineralized | ad 100 g |

The CH-acidic compound (component A) is firstly dissolved with stirring in a small amount of water, then topped up with water to 98 g. With stirring, the Natrosol is added and the desired thickening is awaited.

Aqueous gel formulation for component B Gel 2:

| | |
|---|---|
| Carbonyl compound (component B) | 10 mmol |
| Natrosol HR 250 | 2 g |
| NaOH (50% strength aqueous solution) | possibly a few drops |
| Water, demineralized | ad 100 g |

The carbonyl compound (component B) is dissolved or suspended in a small amount of water. If required, to increase the solubility, the mixture is alkalized with a few drops of 50% strength sodium hydroxide solution. It is then topped up with water to 98 g and stirred until the carbonyl compound dissolves completely (sometimes with gentle heating to about 40° C.). Then, with stirring, the Natrosol is added and the swelling process awaited.

3.0 Colorations

To provide equalizing tresses, human hair tresses from Kerling (0.5 g Kerling, natural white) were tied in the middle and one half was bleached (upper tress section). The other half was bleached twice and subjected to two conventional permanent wave treatments with the commercial product Poly Lock-Normal Permanent Wave (lower tress section). In the course of a permanent wave treatment, the fibers were in each case in a first step exposed for 30 minutes at room temperature to the reducing solution (comprising 7.9% by weight of thioglycolic acid), rinsed with clean water and then neutralized at room temperature for 10 minutes (oxidizing solution comprising 2.6% by weight of hydrogen peroxide). Following the oxidative treatment, the fibers were in each case rinsed again and dried.

Aqueous gel formulations from point 2.0 (gel 1 and gel 2) with the dye precursor combinations in table 1 were prepared. The gels were mixed in the weight ratio 1:1, then the pH was adjusted to a value of 9 using ammonia or tartaric acid. The dye precursors were used in the combinations listed in table 1.

The resulting ready-to-use hair colorant was applied to an equalizing tress (liquor weight ratio: gel mixture to hair=2 to 1) and distributed evenly using an applicette. After a contact time of 30 minutes at 32° C., the tress was rinsed with lukewarm water and then dried in a warm stream of air (30° C. to 40° C.). Relatively intense and brilliant colorations were obtained with the dye precursors according to the invention. The colorations are given in table 1.

Compounds of Component A (Table 1):
A1 1,2-dihydro-1,3,4-trimethyl-2-oxopyrimidinium chloride (not according to the invention)
A2 1,2-dihydro-1,3,4,6-tetramethyl-2-oxopyrimidinium hydrogensulfate (not according to the invention)
A3 1-allyl-1,2-dihydro-3,4,6-trimethyl-2-oxopyrimidinium bromide (according to the invention)
A4 1,2-dihydro-1-(2-hydroxyethyl)-3,4,6-trimethyl-2-oxopyrimidinium p-toluenesulfonate (according to the invention)

Compounds of Component B (Table 1):
B1 4-hydroxy-3-methoxybenzaldehyde (vanillin)
B2 3,5-dimethoxy-4-hydroxybenzaldehyde
B3 4-hydroxy-1-naphthaldehyde
B4 4-hydroxy-2-methoxybenzaldehyde
B5 3,4,5-trihydroxybenzaldehyde
B6 3,4-dihydroxy-5-methoxybenzaldehyde
B7 2,4-dimethoxybenzaldehyde (not according to the invention)
B8 4-hydroxybenzaldehyde (not according to the invention)

TABLE 1

| Component A (gel 1) | Component B (gel 2) | Color shade | According to the invention |
|---|---|---|---|
| A1 | B1 | Violet | No |
| A1 | B7 | Yellow | No |
| A1 | B8 | Orange-red | No |
| A2 | B1 | Violet | No |
| A2 | B2 | Dark blue | No |
| A2 | B4 | Red | No |
| A3 | B1 | Luminous violet | Yes |
| A3 | B2 | Intense dark blue | Yes |
| A3 | B3 | Intense dark blue | Yes |
| A3 | B4 | Luminous red | Yes |
| A3 | B5 | Intense dark blue | Yes |
| A3 | B6 | Intense dark blue | Yes |
| A4 | B1 | Luminous violet | Yes |
| A4 | B2 | Intense dark blue | Yes |
| A4 | B3 | Luminous violet | Yes |
| A4 | B4 | Luminous red | Yes |

4.0 Determination of the Washing Fastness

After the dyeing operation from 3.0, the equalizing tresses were measured colorimetrically using a colorimeter from Datacolor, model Spectraflash 450. Four measurements were made in the upper section of the hair tress, and four measurements in the lower section of the tress. To simulate the washing operation, the hair tresses were introduced for 15 minutes into an ultrasound bath from Elma (model T 790/H, level 5) which was filled with a 1% strength Texapon-NSO-UP solution. After drying, another colorimetric measurement was made as described above.

The dE value used for assessing the washing fastness per tress section arises from the L*a*b* colorimetric values measured on each tress section as follows:

$$dE = [(L_i - L_0)^2 + (a_i - a_0)^2 + (b_i - b_0)]^{1/2}$$

$L_0$, $a_0$ and $b_0$ here are in each case the averages of the calorimetric values determined from the four measurements before the washing experiment, while $L_i$, $a_i$ and $b_i$ are the averaged calorimetric values after the washing experiment.

The worse the washing fastness of a hair color, the greater the dE value. The dE values are summarized in table 2. Compared to the combinations of the prior art, the colorations with the combinations according to the invention of components A and B have better washing fastness.

Compounds of Component A (Table 2):
A1 1,2-dihydro-1,3,4-trimethyl-2-oxopyrimidinium chloride (not according to the invention)
A2 1,2-dihydro-1,3,4,6-tetramethyl-2-oxopyrimidinium hydrogensulfate (not according to the invention)
A3 1-allyl-1,2-dihydro-3,4,6-trimethyl-2-oxopyrimidinium bromide Compounds of Component B (Table 2):
B1 4-hydroxy-3-methoxybenzaldehyde (vanillin)
B2 3,5-dimethoxy-4-hydroxybenzaldehyde
B3 4-hydroxy-1-naphthaldehyde
B4 4-hydroxy-2-methoxybenzaldehyde

TABLE 2

| Component A (gel 1) | Component B (gel 2) | dE Upper tress section | dE lower tress section | According to the invention |
|---|---|---|---|---|
| A1 | B1 | 9.3 | 34.3 | No |
| A2 | B1 | 3.5 | 4.0 | No |

TABLE 2-continued

| Component A (gel 1) | Component B (gel 2) | dE Upper tress section | dE lower tress section | According to the invention |
|---|---|---|---|---|
| A2 | B2 | 4.8 | 4.1 | No |
| A2 | B4 | 7.9 | 2.0 | No |
| A3 | B1 | 1.8 | 1.7 | Yes |
| A3 | B2 | 1.6 | 2.5 | Yes |
| A3 | B3 | 3.7 | 5.6 | Yes |
| A3 | B4 | 1.1 | 1.7 | Yes |

5.0 Determination of the Light Fastness

After the dyeing according to point 3.0, the hair tress was exposed for 120 hours to irradiation with a Xenon burner in accordance with DIN 54004 (color temperature 5500-6500 K; wavelength ranges: UV range=300-400 nm; V is range=400-700 nm). After this treatment, the tress was assessed visually under a daylight lamp. The color intensity was graded with a value between 1 and 6. Value 6 here means very good light fastness, at a value of 1, the light fastness is classed as very poor. The assessment of the light fastnesses is summarized in table 3. The colorations according to the invention have greatly improved light fastnesses.

TABLE 3

| Component A (gel 1) | Component B (gel 2) | Light fastness | According to the invention |
|---|---|---|---|
| A1 | B7 | 1-2 | No |
| A1 | B8 | 1-2 | No |
| A3 | B5 | 5-6 | Yes |
| A3 | B6 | 6 | Yes |

Compounds of Component A (Table 3):
A1 1,2-dihydro-1,3,4-trimethyl-2-oxopyrimidinium chloride (not according to the invention)
A3 1-allyl-1,2-dihydro-3,4,6-trimethyl-2-oxopyrimidinium bromide Compounds of Component B (Table 3):
B5 3,4,5-trihydroxybenzaldehyde
B6 3,4-dihydroxy-5-methoxybenzaldehyde
B7 2,4-dimethoxybenzaldehyde (not according to the invention)
B8 4-hydroxybenzaldehyde (not according to the invention)

What is claimed is:
1. A composition comprising:
(i) at least one component selected from the group consisting of salt compounds of general formula I, enamine counterparts of salt compounds of general formula I, and mixtures thereof:

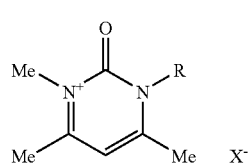

(I)

wherein each Me represents a methyl group, R represents a substituent selected from the group consisting of an allyl group, a hydroxy-($C_{2-6}$)-alkyl group, a benzyl group, and substituted benzyl groups, and $X^-$ represents a physiologically compatible anion; and
(ii) at least one aldehyde selected from the group consisting of 4-hydroxy-3-methoxybenzaldehyde, 3,5-dimethoxy-4-hydroxybenzaldehyde, 4-hydroxy-1-naphthaldehyde, 4-hydroxy-2-methoxybenzaldehyde, 3,4-dihydroxy-5-methoxybenzaldehyde, 3,4,5-trihydroxybenzaldehyde, 3,5-dibromo-4-hydroxybenzaldehyde, 4-hydroxy-3-nitrobenzaldehyde, 3-bromo-4-hydroxybenzaldehyde, 4-hydroxy-3-methylbenzaldehyde, 3,5-dimethyl-4-hydroxybenzatdehyde, 5-bromo-4-hydroxy-3-methoxybenzaldehyde, 4-diethyl-amino-2-hydroxybenzaldehyde, 4-dimethylamino-2-methoxybenzaldehyde, and mixtures thereof.

2. The composition according to claim 1, wherein R represents a substituent selected from the group consisting of an allyl group, a 3-hydroxypropyl group, a 2-hydroxypropyl group, a 2-hydroxyethyl group, and a benzyl group.

3. The composition according to claim 1, wherein $X^-$ represents a physiologically compatible anion selected from the group consisting of a halide, a benzenesulfonate, a p-toluenesulfonate, a $C_{1-4}$-alkanesulfonate, a trifluoromethanesulfonate, a perchlorate, a 0.5 sulfate, a hydrogensulfate, a tetrafluoroborate, a hexafluorophosphate, and a tetrachlorozincate.

4. The composition according to claim 1, wherein the at least one component (i) comprises a physiologically compatible salt or counterpart enamine form of a compound selected from the group consisting of: 1-allyl-1,2-dihydro-3,4,6-trimethyl-2-oxopyrimidinium; 1,2-dihydro-1-(2-hydroxyethyl)-3,4,6-trimethyl-2-oxopyrimidinium; 1,2-dihydro-1-(3-hydroxypropyl)-3,4,6-trimethyl-2-oxopyrimidinium; 1-benzyl-1,2-dihydro-3,4,6-trimethyl-2-oxopyrimidinium, and mixtures thereof.

5. The composition according to claim 1, further comprising at least one additional component selected from the group consisting of CH-acidic compounds different from the at least one component (i), reactive carbonyl compounds different from the at least one aldehyde, and mixtures thereof.

6. The composition according to claim 1, further comprising a physiologically compatible salt of a compound selected from the group consisting of 1,4-dimethylquinolinium, 1-ethyl-4-methylquinolinium, 1-ethyl-2-methylquinolinium, 1,2,3,3-tetramethyl-3H-indolium, 2,3-dimethylbenzothiazolium, 2,3-dimethylnaphtho[1,2-d]thiazolium, 3-ethyl-2-methylnaphtho[1,2-d]thiazolium, 3-ethyl-2-methylbenzoxazolium, 1,2,3-trimethylquinoxalinium, 3-ethyl-2-methylbenzothiazolium, 1,2-dihydro-1,3,4,6-tetramethyl-2-oxopyrimidinium, 1,2-dihydro-1,3,4-trimethyl-2-oxopyrimidinium, 1,2-dihydro-4,6-dimethyl-1,3-dipropyl-2-oxopyrimidinium, 1,2-dihydro-1,3,4,6-tetramethyl-2-thioxopyrimidinium, 1,2-dihydro-1,3,4,5,6-pentamethyl-2-oxopyrimidinium, 2,5-dimethyl-3-(2-propenyl)-1,3,4-thiadiazolium, 3-ethyl-2,5-dimethyl-1,3,4-thiadiazolium, 1,2-dimethylquinolinium and 1,3,3-trimethyl-2-methyleneindoline (Fischer's base), oxindole, 3-methyl-1-phenylpyrazolin-5-one, indane-1,2-dione, indane-1,3-dione, indan-1-one, 2-amino-4-imino-1,3-thiazoline hydrochloride, benzoylacetonitrile, 3-dicyanomethyleneindan-1-one, 2-(2-furanoyl)acetonitrile, 2-(2-theonyl)acetonitrile, 2-(cyanomethyl)benzimidazole, 2-(cyanomethyl)benzothiazole, 2-(2,5-dimethyl-3-furanoyl)acetonitrile, and mixtures thereof.

7. The composition according to claim 1, further comprising a reactive carbonyl compound selected from the group consisting of coniferylaldehyde, 2-methoxybenzaldehyde, 3-methoxybenzaldehyde, 4-methoxybenzaldehyde, 2-ethoxybenzaldehyde, 3-ethoxybenzaldehyde, 4-ethoxybenzaldehyde, 4-hydroxy-2,3-dimethoxybenzaldehyde, 4-hydroxy-2,5-dimethoxybenzaldehyde, 4-hydroxy-2,6-dimethoxybenzaldehyde, 4-hydroxy-2-methylbenzaldehyde, 4-hydroxy-2,3-dimethylbenzaldehyde, 4-hydroxy-2,5-dimethylbenzaldehyde, 4-hydroxy-2,6-dimethylbenzaldehyde, 3,5-diethoxy-4-hydroxybenzaldehyde, 2,6-diethoxy-4-hydroxybenzaldehyde, 3-hydroxy-4-methoxybenzaldehyde, 2-hydroxy-4-methoxybenzaldehyde, 2-ethoxy-4-hydroxybenzaldehyde, 3-ethoxy-4-hydroxy-benzaldehyde, 4-ethoxy-2-hydroxybenzaldehyde, 4-ethoxy-3-hydroxybenzaldehyde, 2,3-dimethoxybenzaldehyde, 2,4-dimethoxybenzaldehyde, 2-5-dimethoxybenzaldehyde, 2,6-dimethoxybenzaldehyde, 3,4-dimethoxybenzaldehyde, 3,5-dimethoxybenzaldehyde, 2,3,4-trimethoxybenzaldehyde, 2,3,5-trimethoxybenzaldehyde, 2,3,6-trimethoxybenzaldehyde, 2,4,6-trimethoxybenzaldehyde, 2,4,5-trimethoxybenzaldehyde, 2,5,6-trimethoxybenzaldehyde, 2-hydroxybenzaldehyde, 3-hydroxybenzaldehyde, 4-hydroxybenzatdehyde, 2,3-dihydroxybenz-aldehyde, 2,4-dihydroxybenzaldehyde, 2,4-dihydroxy-3-methylbenzaldehyde, 2,4-dihydroxy-5-methylbenzaldehyde, 2,4-dihydroxy-6-methylbenzaldehyde, 2,4-dihydroxy-3-methoxybenzaldehyde, 2,4-dihydroxy-5-methoxybenzaldehyde, 2,4-di-hydroxy-6-methoxybenzaldehyde, 2,5-dihydroxybenzaldehyde, 2,6-dihydroxybenzaldehyde, 3,4-dihydroxybenzaldehyde, 3,4-dihydroxy-2-methylbenzaldehyde, 3,4-di-hydroxy-5-methylbenzaldehyde, 3,4-dihydroxy-6-methylbenzaldehyde, 3,4-dihydroxy-2-methoxybenzaldehyde, 3,5-dihydroxybenzaldehyde, 2,3,4-trihydroxy-benzaldehyde, 2,3,5-trihydroxybenzaldehyde, 2,3,6-trihydroxybenzaldehyde, 2,4,6-trihydroxybenzaldehyde, 2,4,5-trihydroxybenzaldehyde, 2,5,6-trihydroxybenzaldehyde, 4-dimethylaminobenzaldehyde, 4-diethylaminobenzaldehyde, 4-dimethylamino-2-hydroxybenzaldehyde, 4-pyrrolidinobenzaldehyde, 4-morpholinobenzaldehyde, 2-morpholinobenzaldehyde, 4-piperidinobenzaldehyde, 3,5-dichloro-4-hydroxybenzaldehyde, 4-hydroxy-3,5-diiodobenzaldehyde, 3-chloro-4-hydroxybenzatdehyde, 5-chloro-3,4-dihyroxy-benzaldehyde, 5-bromo-3,4-dihydroxybenzaldehydro, 3-chloro-4-hydroxy-5-methoxy-beuzaldehyde, 4-hydroxy-3-iodo-5-methoxybenzaldehyde, 2-methoxy-1-naphthaldehyde, 4-methoxy-1-naphthaldehyde, 2-hydroxy-1-naphthaldehyde, 2,4-dihydroxy-1-naphthaldehyde, 4-hydroxy-3-methoxy-1-naphthaldehyde, 2-hydroxy-4-methoxy-1-naphthaldehyde, 3-hydroxy-4-methoxy-1-naphthaldehyde, 2,4-dimethoxy-1-naphthaldehyde, 3,4-dimethoxy-1-naphthaldehyde, 4-dimethylamino-1-naphthaldehyde, 2-nitrobenzaldehyde, 3-nitrobenzaldehyde, 4-nitrobenzaldehyde, 4-methyl-3-nitrobenzaldehyde, 3-hydroxy-4-nitro-benzaldehyde, 5-hydroxy-2-nitrobenzaldehyde, 2-hydroxy-5-nitrobenzaldehyde, 2-hydroxy-3-nitrobenzaldehyde, 2-fluoro-3-nitrobenzaldehyde, 3-methoxy-2-nitrobenzaldehyde, 4-chloro-3-nitrobenzaldehyde, 2-chloro-6-nitrobenzaldehyde, 5-chloro-2-nitrobenzaldehyde, 4-chloro-2-nitrobenzaldehyde, 2,4-dinitrobenzaldehyde, 2,6-dinitrobenzaldehyde, 2-hydroxy-3-methoxy-5-nitrobenzaldehyde, 4,5-dimethoxy-2-nitrobenzaldehyde, 6-nitro-piperonal, 2-nitropiperonal, 5-nitrovanillin, 2,5-dinitrosalicylaldehyde, 5-bromo-3-nitrosalicylaldehyde, 4-nitro-1-naphthaldehyde, 2-nitrocinnamaldehyde, 3-nitrocinnamaldehyde, 4-nitrocinnamaldehyde, 4-dimethylaminocinnamaldehyde, 2-dimethylaminobenzaldehyde, 2-chloro-4-dimethylaminobenzaldehyde, 4-dimethylamino-2-methylbenzaldehyde, 4-diethylaminocinnamaldehyde, 4-dibutyl-aminobenzaldehyde, 4-diphenylaminobenzaldehyde, 4-(1-imidazolyl)benzaldehyde, piperonal, and mixtures thereof.

8. The composition according to claim 1, wherein the at least one component (i) and the at least one aldehyde are each present in an amount of 0.03 to 65 mmol per 100 g of the composition.

9. The composition according to claim 1, further comprising a color enhancer selected from the group consisting of piperidine, piperidine-2-carboxylic acid, piperidine-3-carboxylic acid, piperidine-4-carboxylic acid, pyridine, 2-hydroxypyridine, 3-hydroxypyridine, 4-hydroxypyridine, imidazole, 1-methylimidazole, arginine, histidine, pyrrolidine, proline, pyrrolidone, pyrrolidone-5-carboxylic acid, pyrazole, 1,2,4-triazole, piperazidine, and mixtures thereof.

10. The composition according to claim 1, further comprising an oxidizing agent.

11. The composition according to claim 1, further comprising at least one developer component.

12. The composition according to claim 1, further comprising at least one direct dye present in an amount of 0.01 to 20% by weight, based on the composition.

13. The composition according to claim 1, further comprising a surfactant selected from the group consisting of anionic surfactants, zwitterionic surfactants, nonionic surfactants and mixtures thereof.

14. A method comprising:
(a) providing at least one component selected from the group consisting of salt compounds of general formula I, enamine counterparts of salt compounds of general formula I, and mixtures thereof:

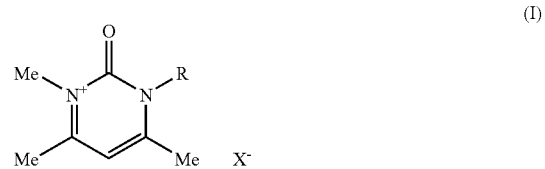

(I)

wherein each Me represents a methyl group, R represents a substituent selected from the group consisting of an allyl group, a hydroxy-($C_{2-6}$)-alkyl group, a benzyl group, and substituted benzyl groups, and $X^-$ represents a physiologically compatible anion;
(b) providing at least one aldehyde selected from the group consisting of 4 hydroxy-3-methoxybenzaldehyde, 3,5-dimethoxy-4-hydroxybenzaldehyde, 4-hydroxy-1-naphthaldehyde, 4-hydroxy-2-methoxybenzaldehyde, 3,4-dihydroxy-5-methoxybenzaldehyde, 3,4,5-trihydroxybenzaldehyde, 3,5-dibromo-4-hydroxybenzaldehyde, 4-hydroxy-3-nitrobenzaldehyde, 3-bromo-4-hydroxybenzaldehyde, 4-hydroxy-3-methylbenzaldehyde, 3,5-dimethyl-4-hydroxybenzaldehyde, 5-bromo-4-hydroxy-3-methoxybenzaldehyde, 4-diethyl-amino-2-hydroxybenzaldehyde, 4-dimethylamino-2-methoxybenzaldehyde, and mixtures thereof;
(c) contacting a keratinic fiber with the at least one component and the at least one aldehyde; and
(d) removing the at least one component and the at least one aldehyde from the keratinic fiber.

15. The method according to claim 14, wherein the at least one component and the at least one aldehyde are applied to the keratinic fiber simultaneously.

16. The method according to claim 14, wherein the at least one component and the at least one aldehyde are applied to the keratinic fiber sequentially.

17. The method according to claim 14, wherein R represents a substituent selected from the group consisting of an allyl group, a 3-hydroxypropyl group, a 2-hydroxypropyl group, a 2-hydroxyethyl group, and a benzyl group.

18. The method according to claim 14, wherein the at least one component comprises a physiologically compatible salt or counterpart enamine form of a compound selected from the group consisting of: 1-allyl-1,2-dihydro-3,4,6-trimethyl-2-oxopyrimidinium; 1,2-dihydro-1-(2-hydroxyethyl)-3,4,6-trimethyl-2-oxopyrimidinium; 1,2-dihydro-1-(3-hydroxypropyl)-3,4,6-trimethyl-2-oxopyrimidinium; 1-benzyl-1,2-dihydro-3,4,6-trimethyl-2-oxopyrimidinium, and mixtures thereof.

19. The method according to claim 14, further comprising pretreating the keratinic fiber prior to contact with the at least one component and the at least one aldehyde, wherein pretreating the keratinic fiber comprises contacting the keratinic fiber with an agent selected from the group consisting of bleaching agents, oxidation colorants and combinations thereof.

20. A compound according to general formula I:

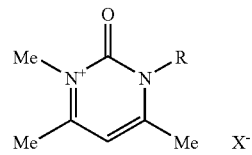

(I)

wherein each Me represents a methyl group, R represents a substituent selected from the group consisting of an allyl group, a hydroxy-$(C_{2-6})$-alkyl group, a benzyl group, and substituted benzyl groups, and $X^-$ represents a physiologically compatible anion.

* * * * *